US006518044B1

(12) United States Patent
Berka et al.

(10) Patent No.: US 6,518,044 B1
(45) Date of Patent: Feb. 11, 2003

(54) PROMOTERS FOR EXPRESSING GENES IN A FUNGAL CELL

(75) Inventors: Randy M. Berka, Davis, CA (US); Michael W. Rey, Davis, CA (US); Kimberly Brown, Elk Grove, CA (US); Stephen H. Brown, Davis, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/999,201

(22) Filed: Oct. 30, 2001

Related U.S. Application Data

(60) Division of application No. 09/534,407, filed on Mar. 22, 2000, now Pat. No. 6,361,973, which is a continuation-in-part of application No. 09/274,449, filed on Mar. 22, 1999, now abandoned.
(60) Provisional application No. 60/145,339, filed on Jul. 22, 1999.

(51) Int. Cl.[7] .......................... C12P 21/02; C12N 15/11
(52) U.S. Cl. ...................................... 435/69.1; 536/24.1
(58) Field of Search ......................... 435/69.1; 536/24.1

(56) References Cited

U.S. PATENT DOCUMENTS 5,837,847 A 11/1998 Royer et al.

FOREIGN PATENT DOCUMENTS

WO WO 96/00787 1/1996
WO WO 97/26330 7/1997

*Primary Examiner*—Terry McKelvey
(74) *Attorney, Agent, or Firm*—Robert L. Stames

(57) ABSTRACT

The present invention relates to methods for producing a polypeptide, comprising: (a) cultivating a fungal host cell in a medium conducive for the production of the polypeptide, wherein the fungal host cell comprises a first nucleic acid sequence encoding the polypeptide operably linked to a second nucleic acid sequence comprising a promoter foreign to the nucleic acid sequence, wherein the promoter comprises a sequence selected from the group consisting of nucleotides 1 to 3949 of SEQ ID NO:1, nucleotides 1 to 938 of SEQ ID NO:2, and nucleotides 1 to 3060 of SEQ ID NO:3, and a subsequence thereof; and mutant, hybrid, and tandem promoters thereof; and (b) isolating the polypeptide from the cultivation medium. The present invention also relates to the isolated promoter sequences and to constructs, vectors, and fungal host cells comprising the promoter sequences operably linked to nucleic acid sequences encoding polypeptides.

20 Claims, 24 Drawing Sheets

```
AATTTCGTCGATAGCGAGGGACTCCTGGCCCTCGAATTTAGTTAGCGTATCAGTGTAAAG 60
TGCTGGGTTCTCCAGGCGTAAGTAAATTGAACCAGATGTTAGCTCCCAGATTTCGCCCCG 120
AAGCCGGTTGGGCAGACCAACGCGGATAAGTTTATGGAAAGTTGGTTGGCGGATCAATGT 180
AAAGTTCCTGCCATTGTCACGCAGATACTCGGCCCAAAGACGCATCTTTGCCCTATCGCG 240
CAACTTTTTGGGTCCCCAGGATATCGGAAGAGCATTCCTAAGCCAGCATCTGGTGGGAG 300
ATCGTTCTTCTTATCTTCGGTTCTTAAAAGATGTTCAGAGTAACACTCAGCAGCAACTCG 360
ACGCAACTTGGCTACGTTGCCAACGCCTGCTCTAAGACCCTTCTTGAGGCCGTCACAGAA 420
ACGTTCGCAGGACTGTCTGGTTCCAGCGAGATGGATTGTTATGCGTTGTTCTCGGGGGTC 480
TCTCTTGTCTTTAGAGGTATCGGCAAGAAGGCCATTCCACGTAGTCAGAGCGAGTGCGAA 540
CTATAACCAGGCAACGTCAGAATTTGTACCATGCAAGATTTTTATACCACATACCTGGAA 600
GTTCTGGCTATTCAAGCGCTCTACCCTTCGTATAGCACATAAAGGAAATGTGAATCCATT 660
GCCACTGGGTCCTCCTCCGTGTGTCTGGCCGGTAAAAGCGGTCGAGGTTGAAAGGCTAGC 720
AGATTGCACAAAGCTAGTGGGTGTTGTTGAGAAGCACATGTAATGCTCTGACAGGTGTAG 780
CTTGCCAGCATAATGCCATCCTCGATCGTGATCCTTATCACCGTGAGTAGCGTTGGAGGG 840
CGGGATAGTAAGCTCGGCGTTGATCTCGTAGAGGGGCGCCTGAGAGGCGGGCAAGCGAAA 900
TTGGCTCTGAAATAGCGATGACTTTGAGGGATTCCGATCTGAACTGGATAGATTGAGCCC 960
CTGGGTAGGATCGATAAGCTGCTGGGCTTTTTGAACGATGTTGGTGAAGTTCGAAAACAT 1020
GATTTCGGTCAGCGGCGCATGACGAGGGGGGTTCCGGTCCAGGAGGGAGGTCGCGGCTGA 1080
GCTTGAAGGAGATGCAAGACACGAAGCGAAAGACACGAAGAGAGCGCAAGAGTCTGAGTA 1140
TGTGCAACCAGGCTCGAATAAGTGCAAGGCAGGCAGAAGTACGGAATAGACGATAGAATT 1200
GAGTATAGAAAGGCTGAATGGAAGATGGAGACGAGTTATAGGACGGTGGAGATAGAGTGG 1260
AGTTGAAGTTGAACGAAGCTGCGTCAGGTCCAGATACGGGAGACTGGCCATCAACTACTG 1320
GCCAGGTAGCCAGGGCGCGATGGGCGGGTGGGCAGGGTCGCGGGGGGACCTCAGGGCAT 1380
TCCTTTCTCCAAGGGCCGCTGGGGCTATGGACGGGGCTGGCTGAACTCCAGCCGTCATGG 1440
```

Fig. 1A

```
GATAGCGGTGCAAGAGATCAGGTACTAAGTCTACCATGATAATTTAGGGGGCAGAGAAAA 1500
ATGATATATTTGTTTAGTAGTAAGCGGGTTTTTACAGTTGAGGAACCAACCTTCTTCATT 1560
TATTTATTCTTTCTTTCTCTGCAATTCAGTCCTTTTTCTTAAATAGAATATCTACCAATG 1620
GAACGGCGTGGCTGAAGTGGCTGAAGAATATAGCTCGAGCTGTCAAACCGCTCATCCTAC 1680
TACCCTAGGTATAAAGCTGGGAACTAAGACTCATTTCTATCCAACTCATCATATTGGGAG 1740
TTAGTGTAGACCTGTCGGCCTAGAGAATATGTGTATCTGCATACTTTCAAATACCCTACG 1800
TATACCCACTATGTTTAGCACAATCATTGACCTCTCAAGGCCTCACCCATCTCAACACCT 1860
GTCGTGTGCTCACTTGACTACTTCTTTGAACCAGCTCGCCATCGGACTAGTCGAACAAGC 1920
TTGTCGCCCCCATACAGATGAATGTATGTTTAAAGCTACATGATCAGCCTGAACCGAGCA 1980
TAACTCGAGTGCCGAGACTCCTCTGATGTATATCGAGATGAATGACAAACCTACGGGTCC 2040
GTTCTTGAGAAGTGGCCTGAGATTTCTCACTTGGTGAGAAAAAGGACGGGCGAGCGGGAG 2100
CCTGAGTCAGAAGAAATACCTGTCTCCTTGGATCTCACATGACGGTGTTGTGGAAGAGTG 2160
CATCTATTGTCATTGCTGGAGTGACGGCAGAGTAGGGGTCTAAAGAAACCCATACTGAGT 2220
AGAGATGGAGAAGACAACAAAAGCCCAAGACGACAGAGACGACAGAAGATTAAAGCTATC 2280
AGAGCGAGACTATATCACTATTCGAAACCTGCGAGTAATTTAACAAGAAGTACACATCAT 2340
CATTGTTATCAATTCGACGAAGACATGGTCGAAAATTCTTGCGGTGTATATGTCTGTTGT 2400
ATATGGGCCTGGGCATTGTTATTTTTCGCCGTCTTTATGTGTACTAACACTTCCATTGAT 2460
ACCCCAGAACAAAAGATGAACGCTTAAACAGCACCAAAATCAGGAGAAGAATGGCGCTGC 2520
TCTAGGTATGCTTCTGGGATAAAAAGCGATGTTGATACCTCTCAGAAAAGAAGTGATTTG 2580
AAGTTGAATCAAACAAATAGCCGATGGAGCGATCTGAAGGGGTGGCAGACCTGCTACGCG 2640
CATTTAGGCAAGGCATCAACTCGGCAGATGATTAAGAAAGGTTTTGTAGGTTCACGTGTT 2700
GTGTTGTGTTCCATTATAAGTTTATAACCTTGCTAAGATGCAACGACTCTGACCTCAGGG 2760
TGTTAGAAAAATTGACCACTAGGAGCATAAGTGACGAAATTCGGGGATCAAGACAATAGA 2820
TAGTTTCATTTTCATGTGCTCCTACGTCTTTTCACGTAATGTTTCTTATAAAAAAAAAGA 2880
```

Fig. 1B

```
TAGCATTGTCTCTTTGGTGAAAAGAGAAAAAAAGATGTTACGACGTGGCCTTGATTCGAA 2940
CAGACGCCTCCGAAGAGAATAGATTTCTAGTCTATCGCGTTAGACCACTCCGCCACCACG 3000
CCTTACGTAATCTGTGATTGTTGAAAGTTACTCTCGTGTTACGGTCTATACGTGAAGAAT 3060
CTACACTTGACGAGTCTCGAGGTCTGGGGTCAGTTAGACGGAAATGGGAGAACAAAGAGA 3120
CTTGGTGACATTGCAGGCAACCGGGTAGATGTTGAGGTCATTGATCGGACAAGATTGTTG 3180
CTTCAAAAGTAACAGGTATTCTTTTTTTTAATCAACAGAAACGTTCCATGTTCATTTGTT 3240
AATCCAATCTATTTGTGATAGCGTTTGATGACAAACAATAATAATGATGGTCTGGCGGCT 3300
AGTGATCGTTTGTAATGACGTCGTCATATATCCTATCACTATACAGTTGCTTTGCACACG 3360
CACTCACGTCCTTCATTCGTTGTCTTCACTATTTGATGGTGATTTGGTTCAACAACCTAC 3420
AGAAATAATGACCTGTGGTGTTCTCCGAATATGGCTAGACCAACACAAGCTTGTACCGCG 3480
GCATTCAAATCACCATGTGATGCCCATCATCAGATCATCCACCAACCCAAAAACAGACCA 3540
ACTACTCACAAAAAGGCATCTCATCAAGAAAAAACGGCCAACTAACGTCCAAAAGGCCCG 3600
AAAAACGTCCATCACGCCGCAGCCGAGACTTCAATAGACTGCACAAGAAGGACCGATGAG 3660
ATCGACCAGACTAAACCCGGGAGAGTGTCAAATATGCGGGGGATTGGGGAACTTACCCCA 3720
GAAAAGAGAAGGAGGATAAATTCCATGTCTGGGGTTGACGTCTCTATTGGTTAGACACGA 3780
ACGCCTGCTCTCGGCGTAATTTATACCATAGCGCCAATGAGGGCGGAAACTCCTGTTTTG 3840
TCAAGTCGTCATTGTTGGTTGGGTCATGATATATAGCCAGTAGGTATCCGTCTTGGTGAT 3900
TGACCAGACATATCGCTCATCACAGATCAACATCACTGCTATCACCAACATGCTTACTCA 3960
                                                M  L  T  Q
AGTCCTTTATGGCTTGGTAGCCAGTGCCCTTTGGCAAGGCCAAGTCGTTGCATCACCAAG 4020
 V  L  Y  G  L  V  A  S  A  L  W  Q  G  Q  V  V  A  S  P  S
CAAGGACAATTCACTGGAGCGCTTCATTGACAAACAAGCTGATATTTCTATCAAGGGTGT 4080
 K  D  N  S  L  E  R  F  I  D  K  Q  A  D  I  S  I  K  G  V
CCTTGCTAATATTGGCGCTGATGGAAAAAGGGCACAGGGTGCAGCGCCTGGTGCTGTTGT 4140
 L  A  N  I  G  A  D  G  K  R  A  Q  G  A  A  P  G  A  V  V
```

Fig. 1C

```
GGCAAGTCCATCGAAAGAAGATCCTGATTgtaagccagcatcctaccttgtccttgtccg 4200
 A  S  P  S  K  E  D  P  D
catgctaatgatggtctcagATTGGTACACTTGGACTCGTGACTCTGCTTTAACGTACAA 4260
                    Y  W  Y  T  W  T  R  D  S  A  L  T  Y  K
AGTGCTCGTTGAGAGATTCATCCACGGCGACAAATCTCTCCAACGAAAGATAGATGAATA 4320
 V  L  V  E  R  F  I  H  G  D  K  S  L  Q  R  K  I  D  E  Y
TGTCTCCGCACAAGCGAAACTGCAAGGGACCACAAATCCATCGGGCAGCCCAGAGTCGGG 4380
 V  S  A  Q  A  K  L  Q  G  T  T  N  P  S  G  S  P  E  S  G
CGGTCTCGGCGAGCCAAAGTTCCATGTGAATCTCACTGCTTTCACTGGATCTTGGGGTCG 4440
 G  L  G  E  P  K  F  H  V  N  L  T  A  F  T  G  S  W  G  R
GCCTCAGCGCGACGGCCCTCCGCTTCGGGCTACCGCCTTGACTCTGTATGCAGAATGGCT 4500
 P  Q  R  D  G  P  P  L  R  A  T  A  L  T  L  Y  A  E  W  L
CATTTCCCACGGCGAAAGATCCAAGGCTTTGAACAAAGTCTGGCCAGTCATCGAGAAGGA 4560
 I  S  H  G  E  R  S  K  A  L  N  K  V  W  P  V  I  E  K  D
CCTTGCGTATACTACCAAGTTCTGGAATCGCACTGGCTATGATCTATGGGAGGAGGTTAA 4620
 L  A  Y  T  T  K  F  W  N  R  T  G  Y  D  L  W  E  E  V  N
TGGATCTTCTTTCTTTACACTTTCGGCTTCGCATCGTGCTCTTGTCGAAGGTGCCGCTCT 4680
 G  S  S  F  F  T  L  S  A  S  H  R  A  L  V  E  G  A  A  L
GGCTAAGAAACTTGGCAAATCTTGTCCTGACTGTGTCACCAACGCTCCTCGCGTTCTGTG 4740
 A  K  K  L  G  K  S  C  P  D  C  V  T  N  A  P  R  V  L  C
CTTCCTTCAGACTTTCTGGACTGGTGGCTACGTTGACTCCAACATTAACGTCAAGGATGG 4800
 F  L  Q  T  F  W  T  G  G  Y  V  D  S  N  I  N  V  K  D  G
TCGCAAGGGTCTCGATGTCAACTCCATCCTCTCGTCCATTCATACATTCGATCCCAACTC 4860
 R  K  G  L  D  V  N  S  I  L  S  S  I  H  T  F  D  P  N  S
```

Fig. 1D

```
CAAGTGCACCGACTCGACGTTCCAGCCTTGTTCACCCAGAGCTCTTGCGAACCACAAGGC 4920
 K  C  T  D  S  T  F  Q  P  C  S  P  R  A  L  A  N  H  K  A
GGTCGTCGATTCTTTCAGGTCAATCTATGGTGTCAACAAGAATAGAGGTCAAGGCAAGGC 4980
 V  V  D  S  F  R  S  I  Y  G  V  N  K  N  R  G  Q  G  K  A
CGCGGCTGTTGGTCGATATAGCGAGGACGTGTACTATGATGGCAACCCTTGGTACCTGGC 5040
 A  A  V  G  R  Y  S  E  D  V  Y  Y  D  G  N  P  W  Y  L  A
CACTCTTGCTGCTGCAGAACAACTCTACGCTGCGGTCTACCAGTGGGATAAGCTTGGCGC 5100
 T  L  A  A  A  E  Q  L  Y  A  A  V  Y  Q  W  D  K  L  G  A
TGTTACTGTTGACGATGTATCTTTGTCTTTCTTCAAGGATATCGTTCCCAAGGTCTCCAA 5160
 V  T  V  D  D  V  S  L  S  F  F  K  D  I  V  P  K  V  S  K
AGGCACTTATGCCAAGAAGACCAAGACATACAAGGAGATCATCAAAGCAGCCAAGACTTA 5220
 G  T  Y  A  K  K  T  K  T  Y  K  E  I  I  K  A  A  K  T  Y
CGCCGACGGCTTTGTCGCTGTCGTGCAGACATACACTCCCAAGGACGGCTCACTAGCTGA 5280
 A  D  G  F  V  A  V  V  Q  T  Y  T  P  K  D  G  S  L  A  E
GCAATTTGACAAGTCAACTGGAGCCCCCAAGTCCGCTGTTCACCTCACCTGGTCCTACGC 5340
 Q  F  D  K  S  T  G  A  P  K  S  A  V  H  L  T  W  S  Y  A
CGCCTTTGTCGCCACAACTGAACGTCGCGACGGCATCATCTCTCCCTCCTGGGGCGAAAG 5400
 A  F  V  A  T  T  E  R  R  D  G  I  I  S  P  S  W  G  E  S
CAGCGCCAACAAGGTCCCCGCCGTGTGTCAAGCTGCCCCAGCATGTGACACAACCATCAC 5460
 S  A  N  K  V  P  A  V  C  Q  A  A  P  A  C  D  T  T  I  T
CTTCAGTGTCAAGAACGTGCAAGTTTCATCCGACCAAAAGGTTTACGTGGTTGGCTCAGT 5520
 F  S  V  K  N  V  Q  V  S  S  D  Q  K  V  Y  V  V  G  S  V
GACTGAGCTTTCTAACTGGTCACCTGATGATGGCATTGCGCTTACGCCATCTAGTTCCGG 5580
 T  E  L  S  N  W  S  P  D  D  G  I  A  L  T  P  S  S  S  G
```

Fig. 1E

```
AGTGTGGAGCGTCAAGGTTAAGATTCCTTCTGATACAAGCTTTGAGTACAAGTATATCAA 5640
  V  W  S  V  K  V  K  I  P  S  D  T  S  F  E  Y  K  Y  I  K
GAAGACTAGCAGTGGGGATGTTACGTGGTTGAGTGATCCCAACAACCGGGCTATTACGGG 5700
  K  T  S  S  G  D  V  T  W  L  S  D  P  N  N  R  A  I  T  G
TAGCAAGTGTGGAAGTACAAGTACTCTTGATGATGAGTGGAGGTAGTGGATGACAGATTT 5760
  S  K  C  G  S  T  S  T  L  D  D  E  W  R  .
ATCAAGCTATGTAGTTTTGTGAATATATAATTATCCAAATTATCAGGGTTCGGTAAGAAT 5820
ATAATTCAGTTCAGCAGTCTGTACAAGCAAGCCATGATTCACGCTTCCTTCGTTTGGAAG 5880
ATAAGGGTTCCTCGCCACCGTCAAGATAATTTTCTCGTGCTAATATCACGTAATCCATCT 5940
GCATTAAACCCTTGCCGGGAAGGTTTCTTCAACCCAGCAACCCCAGAGTAACTCGGAGAT 6000
AGGGAAGTCTATTTGCCTTATCCTCCGTGACGAATTCCCTGAACCCAATT           6050
```

Fig. 1F

```
AATTACTACTGTGATGTGATCACACCTAACTAAATACCTAACTCACCCGATGGATCGACA 60
AGGAAATCTCACGCCCTTGTCGAGTCTCCTCTTTCGTCTGTCTCCTGGGCTCGCTACTGT 120
CCGATTGTAACTCTCGCTCTCCAACTTGTTCAACTCTAATAAGTGGTGGCACAACGTGAA 180
GATGTATTGTTGTGTGAGGCGGGGGGTTGCGTGGCATTACCAAAGAGACCAAAAGTCCCC 240
CTATGTCGATTTGATGGTGTTGCGTTGCCATGATACGGGACCCCGAATATGTTGTATGCA 300
TCATGCGTACAGAAAGCTACTGTTCAAAACGAACGGCAAAGCGGATTGATCAACCCGTGA 360
AAGACCATGGGTCTCTCTCAGTCCACAATCTTCTCTTCCTGATCAAATTTATGGATCCAA 420
GCGGCCACAATTCTAGCGCCATCATGGGTCCCTTTCCTCTTTTCGCTCACCCCATGTTCC 480
CTGTCCCACCTCATTCAGTGGACCTGATGGATCCCTATCCCCCGATGAGCCGGGGGGTGC 540
AGCCTTGGCGCTCTCTTCTTGTTAGTGTGACCTACTGTTGATTTCACTCAGCAGTCCTAG 600
AGTCCATTTAGTTGGGCCTGGGGTGATGGGGTCTGAGACTTTGCTTCTTGCCTGGTCTTG 660
TCTAGCTCGAATCTGTGGGTTGCCTGGCCTGGCCTGGCCTGACCTGACCTGAGGGGGGTG 720
CCCCTTTGCTCTGTTCTGCATATGTTGCTATTAGCTACCTACTCGAGAATTCATAAAAGG 780
ACTGTCCAGCCCCGTCTCTTACTGACTTCTTTCCTTTCCCTCTTCACCCTCGTTGTCATA 840
TCAAATCTGTCACTCGTTAGACCAGACTACCATTCCCACTTTCGCTTTTAAACTACTTTA 900
CTCAACTAATTCTAATACCAACTCCAAAAACCATCAACATGCGTTTCACATCAATCCTCG 960
                                      M  R  F  T  S  I  L
CTGCCGGCGCTTTCGCCACCATGGCCGCTGCCCAGAGCAAGACCGTCTCCCTCGACCCTG 1020
A  A  G  A  F  A  T  M  A  A  A  Q  S  K  T  V  S  L  D  P
CTCAGCAGTCTCAGGCCGACTGCCTCTCCGACTGTGAGCCTGGCGATGTCAAGTGCCAGT 1080
A  Q  Q  S  Q  A  D  C  L  S  D  C  E  P  G  D  V  K  C  Q
CTTACTGCATCACTgtatgttacaacaacgattcccctgtcatgtgtagaaaactaacaa 1140
S  Y  C  I  T
tcccaatagGTTCCCTCTCCTGACGAGAAGAACATCGAGGAAACCACCAAGTGTTGTTTG 1200
          V  P  S  P  D  E  K  N  I  E  E  T  T  K  C  C  L
```

Fig. 2A

```
CCGCCTGCCCCAAGGGCAAGGGCTCCGAAGGCCGACACTGAGAAGTACACCGTTTGCATG 1260
 P  P  A  P  R  A  R  A  P  K  A  D  T  E  K  Y  T  V  C  M
AACGAGTGTATCGCCGACAACTACTGGAAGTCCGTTGATGGTACCCCCCGTGGCACCGAC 1320
 N  E  C  I  A  D  N  Y  W  K  S  V  D  G  T  P  R  G  T  D
GTCCCCGATGTCAAGAGCAAGGCCTCCGAGGCTGCCTCCTCCGCTGCTGAGAAGGCCACC 1380
 V  P  D  V  K  S  K  A  S  E  A  A  S  S  A  A  E  K  A  T
GCCACCGGTACTGCTGCTGAGTCTGATGCTACCGCCACTGGTGCCTCCGCTACTGAGTCC 1440
 A  T  G  T  A  A  E  S  D  A  T  A  T  G  A  S  A  T  E  S
GAGTCCGGCTCCGACTCCAGCTCCGAGGAGACCGGCTCTGCCTCTGGCACTGCCACTGGT 1500
 E  S  G  S  D  S  S  S  E  E  T  G  S  A  S  G  T  A  T  G
ACCGCTGCTGAGGTCTCCGAGACTGGTAACGCCGCCTCTTCCCTCGTTGGTGGTGTCTCC 1560
 T  A  A  E  V  S  E  T  G  N  A  A  S  S  L  V  G  G  V  S
TTCCTCGGTCTCGTTGCCGCTATCTTCGCTCTGTAAATTGGGTTTCCTGCTTTAGGATAA 1620
 F  L  G  L  V  A  A  I  F  A  L  .
TCTGATTTGGCATGACGGAGAAGGATTTAATGGGTTTTATTACAGCGGTAATGATTGGAG 1680
TTTGGATTTCAAGATGTGACACGTTGGACAGCATGATAAGGCCTACGGGTCTGATCAATT 1740
TCATGGACAAATTTTGTTTTTTTGGGTAATCATTTCGCGTTCACATATGGCTCGGCATAT 1800
GAGCATGAATACAATACCTCTTTTTTGCGCCTCAATTCATTCCAATTTCTTGTGATCTCA 1860
CAGTGATTCAACTTACAAGTTGCGGCGCGACCACTGAGGTCGTGTCTGATGTGGGTCTTC 1920
TGTTTGTGATTGGCTCATGATTCCCAATCGGGTGCTTCAAACGTTAGTTTGTAAACAAGC 1980
GAAATGAGGGTCTTAGGATGCATGTTCAAAGCGCAAAACCCAATTGAATTCAAATGTTAA 2040
AGAATCATCGAGAAGAGCGAGTTACTGAGGTGAATTTGTGCTTTCAACTGTCAATACCTC 2100
CCTCAGAACAAATGAATTGAATTATTATTCACACTCAATGCCCAATATTCTAAACATGTT 2160
CGTTGTAACAGAGTTTTAATTCCTTGACGCCACAATGTTCCTTGGTAATTATCGCGCCTG 2220
TCACATGAACTGGCTCCTGAACTTAAACGTTGGTGACCCAGCAACTCGTTTATCAGGCTT 2280
```

Fig. 2B

```
AGGGTAGCTGTCATACAACAAACAAACTTGTACAATTGATGTTATTGATGAATCATGTAT 2340
AGAAGAGCACAATTGATTTAAACACAGATAAACTGGTCGAACCGATTTTATCAGGTTGTG 2400
TGAACATGCATTGCCGAATCAGAAACCAGAGTAAGACTATCTACAGTTCCATGAAGACAA 2460
TTCACAGACTGCCAGAAAGCAAGGTACTGGAAGCACGAGAGACAAAATTATTGAATT 2517
```

Fig. 2C

```
AATTAGAGAGGTTAGGGATTTCACATGGCCACCAATGGGAAGGAGGCAACCATCTGCACG 60
AGCCCACCAAGTCATCTCCTCAAACTGTGCTGCGACTAAGAATTTGATTCCGGTTCTGGC 120
CTGGCCTTTGTATCAGCTAGGTCATTCTCGACTACCGGAGGCCAGGCTGAAGCAGTCAGT 180
CACGCATTGTCACTTTATCGGTCCTGTCCTCATACGGATACACTAGGCGTCAATGGGCTT 240
CAAACGGAGATCCAGAGATCTCATGAAGAGCATCGACGATAAAGTGAGTGGTTGGGGATA 300
CTGTGCGGTGCCGACCCCAGCGGCAGCCAGGTTCCACCCTTGATTACATGGTTGAAAAGT 360
GGCGTTACTGGGCGAGATCAAATTTGGCATGTATGTTCGTCCAATGACGCGAGCTCTCCA 420
TGTTGCTGCGAGGGTCAGGAACGGACCAGCATGGGATCAGTGAGGTGAAATCCAACCGAG 480
GGAGAGCGAGATCTTTGTGCTCATATCCATGCTGCCATGCTACGTGCCGAACAGGCCAGA 540
TGGCGTTCAACTCAGTCGACCAGGTCCGATGAACGCGGAGCGGTGACGAGATCGAAGCTT 600
CATCTATCGCTTACGGGGTTATGTTCCACTTTCCATTAACGTTTGCGAGTTGCTGTTTGA 660
GAGCCATGTCGAAAGCATGGACCGTGTCACATCTTTCAAGGTAAATCTGGAGGTGGGAAG 720
AAGAATTGCGAGGAACAGGATGGGAGGATAGCAGGCTGACGCGGAAAGCTAGGTAGCTAC 780
CTGGCTGATTACTGGCTAAAGCTGGAGAGCAACTAGGTAATATCAGGCAAAGAGCTCCAA 840
GAGCTATTGGGAGGCTGGCTGATTGTCTCTGGCTGAGACGCAGGAGGAAGGGTTAAAATG 900
GCCGGCAGGCCAAGAAGGGGCTGCAAAACACGGAGTGGATGGTGGGGCCTCCCACATACG 960
GGATTCGGGCTGCGGATCTAACCTCAATTTGGCAAGAGGTAAATAGGACGACATGCAGGC 1020
CCCCTGACATGTAAACAAGACAAGTGGTAAACAAGCCATCAACATCAACAAGAGCGAACA 1080
ATCGACACACCCATGGGGGTGAGATATGGTAGTAAGGCAGAGAGAGATCAGGGCAGCATA 1140
CGTGGGAAAGGGCTGGGCAAGAAAGGACACAACGGATCAACAGAACGCAGCGCTACCGAG 1200
GGAGCAACACAAGTACAGTAACCGCTCACAGAGGCACAACTCGTCCAATCCTGCCCCCGT 1260
CTTCAAAAGCCCAGTTTCGTTCTGAGTCCTGTCCGGTCCCTCTTCTCCTCCTACTCCCTC 1320
CAATTATCGCCATCCACATCGACATCGTCAATTCACAACCTCACCCAGACAAGAAGAAAA 1380
GAACGACTGAAGGCCTTCGCTCGCCATCACCCGATTCTTTTCCATTCTCTTCGACTTTTG 1440
TTTCGTAGGAACAAGAGCCAGAGAACTTCTTGTCATCCTTTCGAATTTCGGAAGGTTGTA 1500
```

Fig. 3A

```
TGAGAAGCTTCTCTCGCGCCAGCAAAAGTCGCAAATCTGGACTTTGAGGCACGCGTCCCC 1560
GTTCCCTTCAGCATCTTCCCATCGACATATCGGGAATCCGAATCCCACACACAGACCGTT 1620
ACCGAAACAAAGATACACGAAGAGGTTGAGATCAAACCCCAACAGCCCGAAGCCGGACGG 1680
GAAGGTGAAATATCTTCTGTCTCCGTCACCGCCGAACAGGTCCCTCCTCCTCGTCAAGAG 1740
CAAGAGTTTATCGAAGAAGAGGTCCATATTACGCGTGAAGAAGAACATTACCACCGTCCC 1800
GGTGTCCAAAAATTCGAGCACGAAGACTTTACTATCCGTGAAGACTCCCGACGgtacgtt 1860
cgattttacatttcctttcatctccatttaggtcgcatctttttcgttactttttggtc 1920
aattacacgggggatacgattttcccacggtcggagaaagccctgcttgctctctatgcc 1980
taggtctgtattctctcatccctctgcgctgatctggccatggagacgtgtgagaacaag 2040
actacaattcatcacatcatttttcgctaggcgaaagcaattaccgttgtccccgacctt 2100
ctcccaaccatcagttttcactttccctttttcttggtctggcttgccttgaccattaccc 2160
accgcgcacggagcgcttcagtccccagccatcccattctcacatcacttctcatatcct 2220
ctcttcacacgcctcacacacccaccccctgcatgctaccatgccaacccacttcagctt 2280
ggctggatacccaatttgctttgcttcctccccggctcactagcgcctctaagcctgctg 2340
gcctgagcaaggcggtggagctatctcaggggccgccgcctcccgttgccatatgatacg 2400
caaacgacttactatagacatccatcagctaacccagacaaatctagACCTCAACCTCCC 2460
TCTCAATACCAACCTTCCCAGTACCACCAACCTTCCCACTACCAACCACCTCCCAAATTC 2520
CAAACTTCTCACACTCACGTAGAGATCGACACCCACCGTCATCCCTACTACTCCACCCCC 2580
ATTGATCTCGCTGAACGTGAATACCGCCAGCGTTACCGCCCTGCCCAAGCTTTTTCCACA 2640
GAAGACCCTTCTTCCCACTCTCATCCTCACTACCAACCTCAAGACAACTTCAAAGCCAAC 2700
AACTACACCGTTGAAGGCCGACCCGCTCCCCAATTCCATTCCTCTGAGAAGACTGAAATC 2760
AACAAGTTTACTGTTGACGAACACTCCTCTCGCCCTCAGTACAACCACACCGAGAAGACC 2820
GAATTCAACAACTACACTGTTGACAGCCGATCTTCCCGTCCTCAATACAACACCTGTGAG 2880
AAGACTGAGATCAACAATTTCACTGTTGACGCCCGCTCTTCCCAGCCACGGTACCGCGAC 2940
ACCAAGACAACTCAAGTCAACAGCTACGCCGTTGACAAGCCCGTTTCTCGTCCATCTTAC 3000
```

Fig. 3B

```
AAGAAGGACGTGAGATTTACTGAACAAACCGTCGAAGCTTCAAAGTCCGACAAGTCCAAG 3060
ATGGGTTACTACGACGACGAGGgtaagtgaaatctgtcacccagcgagcgccatcaagct 3120
 M  G  Y  Y  D  D  E
ctctattcgtgacgcaattcaagctaacccagtcaccagGTTCTTTCCGCAACGGCGGCA 3180
                                         G  S  F  R  N  G  G
TCCACAAGCTCGGTGACAAGTCCCGCGACATTGAGGTTGACATTCGCGAGACTTCTCGTC 3240
I  H  K  L  G  D  K  S  R  D  I  E  V  D  I  R  E  T  S  R
CTGCCAATGACTGCGCTCCCAACACCGTCAGCATCCCCTGCCACCACATCCGTCTGGGTG 3300
P  A  N  D  C  A  P  N  T  V  S  I  P  C  H  H  I  R  L  G
ATTTCCTCATGCTCCAGGGCCGCCCCTGCCAGGTCATCCGCATCTCCACCTCCTCTGCCA 3360
D  F  L  M  L  Q  G  R  P  C  Q  V  I  R  I  S  T  S  S  A
CTGGCCAGTACCGCTACCTTGGTGTCGACCTCTTCACCAAGCAGCTTCATGAGGAGTCTT 3420
T  G  Q  Y  R  Y  L  G  V  D  L  F  T  K  Q  L  H  E  E  S
CTTTCATCTCCAACCCTGCCCCCAGCGTTGTCGTTCAGTCCATGCTCGGCCCTGTCTTCA 3480
S  F  I  S  N  P  A  P  S  V  V  V  Q  S  M  L  G  P  V  F
AGCAGTACCGTGTCCTCGATATGCAGGAGGGTCAGATCGTTGCCATGACCGAGACTGGCG 3540
K  Q  Y  R  V  L  D  M  Q  E  G  Q  I  V  A  M  T  E  T  G
ACGTCAAGCAGGGTCTCCCTGTCATTGACCAGTCCAACCTCTACTCTCGCCTCCACAACG 3600
D  V  K  Q  G  L  P  V  I  D  Q  S  N  L  Y  S  R  L  H  N
CTTTCGAGTCCGGTCGTGGCTCTGTTCGCGTCCTCGTCCTCAACGACGGTGGCCGTGAGC 3660
A  F  E  S  G  R  G  S  V  R  V  L  V  L  N  D  G  G  R  E
TTGCCGTTGACATGAAGGTCATCCACGGCTCTCGCCTGTAAGCGTGTTCAACTGTTTTCT 3720
L  A  V  D  M  K  V  I  H  G  S  R  L  .
GAATTCGGGCAGCCGCTTGCAATGCGACTTCTTCCCAATGTTTAATTGAGTGAAGGGACA 3780
GCACTACCAGTCTCACCTCAACTGTGGGGAGCGGGTCTGGGCTGTCTCTAATCTTACCTG 3840
```

Fig. 3C

```
TACAATGTCAAGTTTCATAGGGGACCTGTTGTGTCAAGATGGTTCGAGTTTTGTTTGTGT 3900
CAAGATTGGATAAATGATATTGGCTAGCTGGAAATACTGGAGTCTTTTGTGTAGATGGGA 3960
GAGTTCTGTACATGAACTATAGTAATTGACAATTGATTCCGCATCTACTTAGCTTTTCAT 4020
TGGTGCTCTATGCCCAACATGTGAATT                                  4047
```

Fig. 3D

PROMOTERS FOR EXPRESSING GENES IN A FUNGAL CELL

CROSS-REFERENCE TO RELATED APPLICATIONS

This application is a divisional of U.S. application Ser. No. 09/534,407, filed Mar. 22, 2000, now U.S. Pat. No. 6,361,973 which is a continuation-in-part of U.S. application Ser. No. 09/274,449, filed Mar. 22, 1999, now abandoned, and claims priority from U.S. provisional application Serial No. 60/145,339, filed Jul. 22, 1999, which applications are fully incorporated herein by reference.

BACKGROUND OF THE INVENTION

1. Field of the Invention

The present invention relates to methods for producing polypeptides. The present invention also relates to isolated promoters and to nucleic acid constructs, vectors, and host cells comprising the promoters operably linked to nucleic acid sequences encoding polypeptides.

2. Description of the Related Art

The recombinant production of a heterologous protein in a fungal host cell, particularly a filamentous fungal cell such as Aspergillus, may provide for a more desirable vehicle for producing the protein in commercially relevant quantities.

Recombinant production of a heterologous protein is accomplished by constructing an expression cassette in which the DNA coding for the protein is placed under the expression control of a promoter, excised from a regulated gene, suitable for the host cell. The expression cassette is introduced into the host cell, usually by plasmid-mediated transformation. Production of the heterologous protein is then achieved by culturing the transformed host cell under inducing conditions necessary for the proper functioning of the promoter contained on the expression cassette.

The development of a new fungal host cell for the recombinant production of proteins generally requires the availability of promoters that are suitable for controlling the expression of the proteins in the host cell. *Fusarium venenatum* has been shown to be useful as a new host cell for such expression (WO 96/00787, WO 97/26330). Moreover, the promoter from the *Fusariuin oxysporum* trypsin-like protease gene has been described which is useful for expressing heterologous genes in *Fusarium venenatum* host cells (U.S. Pat. No. 5,837,847).

However, there is a need in the art for new promoters for controlling the expression of heterologous genes.

It is an object of the present invention to provide improved methods for producing a polypeptide in a fungal host cell and new promoters for such production.

SUMMARY OF THE INVENTION

The present invention relates to methods for producing a polypeptide, comprising: (a) cultivating a fungal host cell in a medium conducive for the production of the polypeptide, wherein the fungal host cell comprises a first nucleic acid sequence encoding the polypeptide operably linked to a second nucleic acid sequence comprising a promoter foreign to the nucleic acid sequence, wherein the promoter comprises a sequence selected from the group consisting of nucleotides 1 to 3949 of SEQ ID NO:1, nucleotides 1 to 938 of SEQ ID NO:2, and nucleotides 1 to 3060 of SEQ ID NO:3, and subsequences thereof; and mutant, hybrid, and tandem promoters thereof; and (b) isolating the polypeptide from the cultivation medium.

The present invention also relates to isolated promoters sequences and to constructs, vectors, and fungal host cells comprising one or more of the promoters operably linked to a nucleic acid sequence encoding a polypeptide.

The present invention also relates to methods for obtaining mutant promoters of nucleotides 1 to 3949 of SEQ ID NO:1, nucleotides 1 to 938 of SEQ ID NO:2, and nucleotides 1 to 3060 of SEQ ID NO:3.

The present invention also relates to isolated nucleic acid sequences, selected from the group consisting of:

(a) a nucleic acid sequence encoding a polypeptide having an amino acid sequence which has at least 65% identity with amino acids 22 to 581 of SEQ ID NO:4, at least 65% identity with amino acids 19 to 200 of SEQ ID NO:5, or at least 65% identity with amino acids 1 to 187 of SEQ ID NO:6;

(b) a nucleic acid sequence having at least 65% homology with nucleotides 4013 to 5743 of SEQ ID NO: 1, at least 65% homology with nucleotides 993 to 1593 of SEQ ID NO:2, or at least 65% homology with nucleotides 3061 to 3678 of SEQ ID NO:3;

(c) a nucleic acid sequence which hybridizes under very low, low, medium, medium-high, high, or very high stringency conditions with (i) nucleotides 4013 to 5743 of SEQ ID NO:1, nucleotides 993 to 1593 of SEQ ID NO:2, or nucleotides 3061 to 3698 of SEQ ID NO:3; (ii) the cDNA sequence contained in nucleotides 4013 to 5743 of SEQ ID NO:1, nucleotides 993 to 1593 of SEQ ID NO:2, or nucleotides 3061 to 3698 of SEQ ID NO:3; (iii) a subsequence of (i) or (ii) of at least 100 nucleotides, or (iv) a complementary strand of (i), (ii), or (iii);

(d) a nucleic acid sequence encoding a variant of the polypeptide having an amino acid sequence of SEQ ID NO:4, SEQ ID. NO. 5, or SEQ ID NO:6 comprising a substitution, deletion, and/or insertion of one or more amino acids;

(e) an allelic variant of (a), (b), or (c); and (f) a subsequence of (a), (b), (c), or (e).

The present invention further relates to constructs, vectors, and recombinant host cells of the nucleic-acid sequences.

BRIEF DESCRIPTION OF THE FIGURES

FIGS. 1A–1F show the genomic DNA sequence and the deduced amino acid sequence of a *Fusarium venenatum* glucoamylase gene (SEQ ID NOs:1 and 4, respectively).

FIGS. 2A–2C show the genomic DNA sequence and the deduced amino acid sequence of a *Fusarium venenatum* gene designated "Daria" (SEQ ID NOs:2 and 5, respectively).

FIGS. 3A–3D show the genomic DNA sequence and the deduced amino acid sequence of a *Fusarium venenatum* gene designated "Quinn" (SEQ ID NOs:3 and 6, respectively).

DETAILED DESCRIPTION OF THE INVENTION

Figure 4:
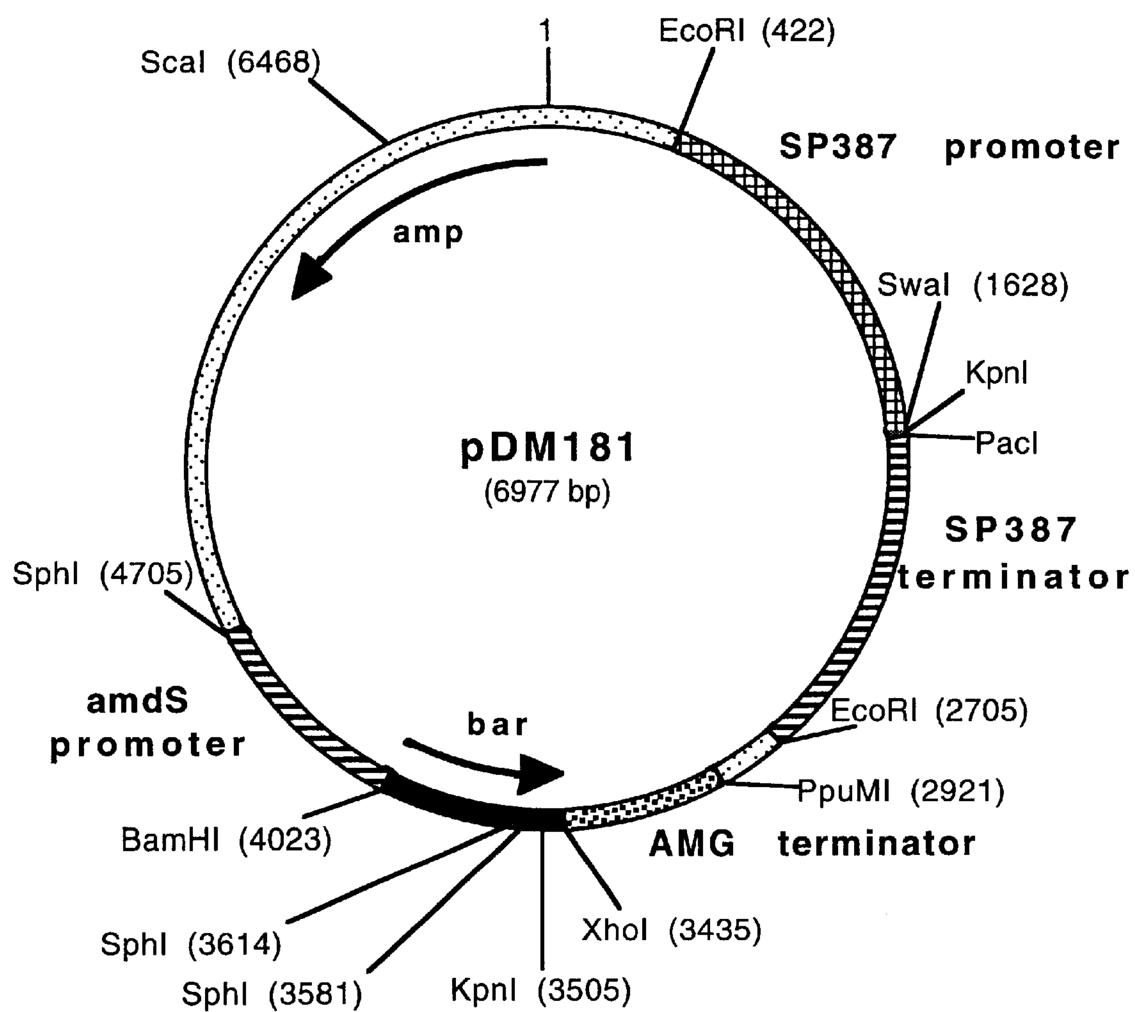
FIG. 4 shows a restriction map of pDM181.

The present invention relates to methods for producing a polypeptide, comprising (a) cultivating a fungal host cell in a medium conducive for the production of the polypeptide, wherein the fungal host cell comprises a first nucleic acid sequence encoding the polypeptide operably linked to a second nucleic acid sequence comprising a promoter foreign to the first nucleic acid sequence, wherein the promoter comprises a sequence selected from the group consisting of nucleotides 1 to 3949 of SEQ ID NO:1, nucleotides 1 to 938 of SEQ ID NO:2, and nucleotides 1 to 3060 of SEQ ID NO:3, and subsequences thereof; and mutant, hybrid, and tandem promoters thereof; and (b) isolating the polypeptide from the cultivation medium.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Promoters

The term "promoter" is defined herein as a DNA sequence that binds RNA polymerase and directs the polymerase to the correct downstream transcriptional start site of a nucleic acid sequence encoding a polypeptide to initiate transcription. RNA polymerase effectively catalyzes the assembly of messenger RNA complementary to the appropriate DNA strand of the coding region. The term "promoter" will also be understood to include the 5' non-coding region (between promoter and translation start) for translation after transcription into mRNA, cis-acting transcription control elements such as enhancers, and other nucleotide sequences capable of interacting with transcription factors.

The term "mutant promoter" is defined herein as a promoter having a nucleotide sequence comprising a substitution, deletion, and/or insertion of one or more nucleotides of a parent promoter, wherein the mutant promoter has more or less promoter activity than the corresponding parent promoter. The term "mutant promoter" will also encompass natural variants and in vitro generated variants obtained using methods well known in the art such as classical mutagenesis, site-directed mutagenesis, and DNA shuffling.

The term "hybrid promoter" is defined herein as parts of two more promoters that are fused together to generate a sequence that is a fusion of the two or more promoters, which is operably linked to a coding sequence and mediates the transcription of the coding sequence into mRNA.

The term "tandem promoter" is defined herein as two or more promoter sequences each of which is operably linked to a coding sequence and mediates the transcription of the coding sequence into mRNA.

The term "operably linked" is defined herein as a configuration in which a control sequence, e.g., a promoter sequence, is appropriately placed at a position relative to a coding sequence such that the control sequence directs the production of a polypeptide encoded by the coding sequence.

The term "coding sequence" is defined herein as a nucleic acid sequence that is transcribed into mRNA which is translated into a polypeptide when placed under the control of the appropriate control sequences. The boundaries of the coding sequence are generally determined by the ATG start codon located just upstream of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences.

In a preferred embodiment, the promoter has the nucleic acid sequence of nucleotides 1 to 3949 of SEQ ID NO:1, or a subsequence thereof. The subsequence preferably contains at least about 2100 nucleotides, more preferably at least about 2400 nucleotides, and most preferably at least about 2700 nucleotides.

In another preferred embodiment, the promoter has the nucleic acid sequence of nucleotides 1 to 938 of SEQ ID NO:2, or a subsequence thereof. The subsequence preferably contains at least about 840 nucleotides, more preferably at least about 870 nucleotides, and most preferably at least about 900 nucleotides.

In another preferred embodiment, the promoter has the nucleic acid sequence of nucleotides 1 to 3060 of SEQ ID NO:3, or a subsequence thereof. The subsequence preferably contains at least about 2100 nucleotides, more preferably at least about 2400 nucleotides, and most preferably at least about 2700 nucleotides.

In another preferred embodiment, the promoter is the nucleic acid sequence contained in plasmid pECO3 which is contained in *Escherichia coli* NRRL B-30067. In another preferred embodiment, the promoter is the nucleic acid sequence contained in plasmid pFAMG which is contained in *Escherichia coli* NRRL B-30071. In another a preferred embodiment, the promoter is the nucleic acid contained in plasmid pQUINN which is contained in *Escherichia coli* NRRL B-30075.

In the methods of the present invention, the promoter may also be a mutant of the promoters described above having a substitution, deletion, and/or insertion of one or more nucleotides in the nucleic acid sequence of nucleotides 1 to 3949 of SEQ ID NO:1, nucleotides 1 to 938 of SEQ ID NO:2, or nucleotides 1 to 3060 of SEQ ID NO:3.

A mutant promoter may have one or more mutations. Each mutation is an independent substitution, deletion, and/or insertion of a nucleotide. The introduction of a substitution, deletion, and/or insertion of a nucleotide into the promoter may be accomplished using any of the methods known in the art such as classical mutagenesis, site-directed mutagenesis, or DNA shuffling. Particularly useful is a procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

In a preferred embodiment, the promoter is a mutant of nucleotides 1 to 3949 of SEQ ID NO:1. In another preferred embodiment, the promoter is a mutant of nucleotides 1 to 938 of SEQ ID NO:2. In another preferred embodiment, the promoter is a mutant of nucleotides 1 to 3060 of SEQ ID NO:3.

In the methods of the present invention, the promoter may also be a hybrid promoter comprising a portion of one or more promoters of the present invention; a portion of a promoter of the present invention and a portion of another promoter, e.g., a leader sequence of one promoter and the transcription start site from the other promoter; or a portion of one or more promoters of the present invention and a portion of one or more other promoters. The other promoter may be any promoter sequence which shows transcriptional activity in the fungal host cell of choice including a mutant, truncated, and hybrid promoter, and may be obtained from genes encoding extracellular or intracellular polypeptides either homologous or heterologous to the host cell. The other promoter sequence may be native or foreign to the nucleic acid sequence encoding the polypeptide and native or foreign to the cell.

Examples of other promoters useful in the construction of hybrid promoters with the promoters of the present invention include the promoters obtained from the genes for *Aspergillus oryzae* TAKA amylase, *Rhizoinucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), *Saccharomyces cerevisiae* enolase (ENO-1), *Saccharomyces cerevisiae* galactokinase (GALI), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase, and mutant, truncated, and hybrid promoters thereof. Other useful promoters for yeast host cells are described by Romanos et al., 1992, *Yeast* 8: 423–488.

The promoter may also be a tandem promoter comprising two more promoters of the present invention or alternatively one or more promoters of the present invention and one or more other promoters, such as those exemplified above. The two or more promoter sequences of the tandem promoter may simultaneously promote the transcription of the nucleic acid sequence. Alternatively, one or more of the promoter sequences of the tandem promoter may promote the transcription of the nucleic acid sequence at different stages of growth of the cell.

In the methods of the present invention, the promoter is foreign to the nucleic acid sequence encoding a polypeptide of interest, but the promoter or nucleic acid sequence may be native to the fungal host cell. A mutant, hybrid, or tandem promoter of the present invention will be understood to be foreign to a nucleic acid sequence encoding a polypeptide even if the wild-type promoter is native to the nucleic acid sequence.

A mutant, hybrid, or tandem promoter of the present invention has at least about 20%, preferably at least about 40%, more preferably at least about 60%, more preferably at least about 80%, more preferably at least about 90%, more preferably at least about 100%, even more preferably at least about 200%, most preferably at least about 300%, and even most preferably at least about 400% of the promoter activity of the promoter of nucleotides 1 to 3949 of SEQ ID NO:1, nucleotides 1 to 938 of SEQ ID NO:2, or nucleotides 1 to 3060 of SEQ ID NO:3.

Polypeptide Encoding Nucleic Acid Sequences

The polypeptide encoded by the nucleic acid sequence may be native or heterologous to the fungal host cell of interest.

The term "polypeptide" is not meant herein to refer to a specific length of the encoded product and, therefore, encompasses peptides, oligopeptides, and proteins. The term "heterologous polypeptide" is defined herein as a polypeptide which is not native to the fungal cell, a native polypeptide in which modifications have been made to alter the native sequence, or a native polypeptide whose expression is quantitatively altered as a result of a manipulation of the fungal cell by recombinant DNA techniques. For example, a native polypeptide may be recombinantly produced by, e.g., placing a gene encoding the polypeptide under the control of a promoter of the present invention to enhance expression of the polypeptide, to expedite export of a native polypeptide of interest outside the cell by use of a signal sequence, and to increase the copy number of a gene encoding the polypeptide normally produced by the cell. The fungal cell may contain one or more copies of the nucleic acid sequence encoding the polypeptide.

Preferably, the polypeptide is a hormone or variant thereof, enzyme, receptor or portion thereof, antibody or portion thereof, or reporter. In a preferred embodiment, the polypeptide is secreted extracellularly. In a more preferred embodiment, the polypeptide is an oxidoreductase, transferase, hydrolase, lyase, isomerase, or ligase. In an even more preferred embodiment, the polypeptide is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, or xylanase.

The nucleic acid sequence encoding a polypeptide of interest may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The techniques used to isolate or clone a nucleic acid sequence encoding a polypeptide of interest are known in the art and include isolation from genomic DNA, preparation from cDNA, or a combination thereof. The cloning of the nucleic acid sequence from such genomic DNA can be effected, e.g., by using the well known polymerase chain reaction (PCR). See, for example, Innis et al., 1990, *PCR Protocols. A Guide to Methods and Application,* Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into the mutant fungal cell where multiple copies or clones of the nucleic acid sequence will be replicated. The nucleic acid sequence may be of genomic, cDNA, RNA, semisynthetic, synthetic origin, or any combinations thereof.

In the methods of the present invention, the polypeptide may also include a fused or hybrid polypeptide in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptide may comprise a combination of partial or complete polypeptide sequences obtained from at least two different polypeptides wherein one or more may be heterologous to the mutant fungal cell.

Nucleic Acid Constructs

The present invention also relates nucleic acid constructs comprising a nucleic acid sequence encoding a polypeptide operably linked to a promoter of the present invention and one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains a coding sequence and all the control sequences required for expression of the coding sequence.

An isolated nucleic acid sequence encoding a polypeptide may be further manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

In the methods of the present invention, the nucleic acid sequence may comprise one or more native control sequences or one or more of the native control sequences may be replaced with one or more control sequences foreign to the nucleic acid sequence for improving expression of the coding sequence in a host cell.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter of the present invention, signal peptide sequence, and transcription terminator. At a minimum, the control sequences include a promoter of the present invention, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum trypsin-like protease.*

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccha-*

*romyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of a gene encoding a polypeptide which is endogenous to a host cell. The constructs may contain the minimal number of components necessary for altering expression of the endogenous gene. In one embodiment, the nucleic acid constructs preferably contain (a) a targeting sequence, (b) a promoter of the present invention, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a promoter of the present invention, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

The present invention further relates to methods for producing a polypeptide comprising (a) cultivating a homologously recombinant cell, having incorporated therein a new transcription unit comprising a promoter of the present invention, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

Expression Vectors

The present invention also relates to recombinant expression vectors comprising a promoter of the present invention, a nucleic acid sequence encoding a polypeptide, and transcriptional and translational stop signals. The various nucleic acid and control sequences described above may be joined together to produce a recombinant expression vector which may include one or more convenient restriction sites to allow for insertion or substitution of the promoter and/or nucleic acid sequence encoding the polypeptide at such sites. Alternatively, the nucleic acid sequence may be expressed by inserting the nucleic acid sequence or a nucleic acid construct comprising the promoter and/or sequence into an appropriate vector for expression. In creating the expression vector, the coding sequence is located in the vector so that the coding sequence is operably linked with a promoter of the present invention and one or more appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof Preferred for use in an Aspergillus cell are the amdS and pyrG genes of *Aspergillus nidulans* or *Aspergillus oryzae* and the bar gene of *Streptomyces hygroscopicus.*

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of origins of replication for use in a yeast host cell are the 2 micron origin of replication, ARS 1, ARS4, the combination of Ars 1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence encoding a polypeptide may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a promoter of the present invention operably linked to a nucleic acid sequence encoding a polypeptide, which are advantageously used in the recombinant production of the polypeptides. A vector comprising a promoter of the present invention operably linked to a nucleic acid sequence encoding a polypeptide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any fungal cell usefull in the methods of the present invention. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In a more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a Saccharomyces carlsbergensis, *Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al, 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearun, Fusarium graminum, Fusarium heterosporum, Fusarium negundi, Fusarium oxysporum, Fusarium reticulatum, Fusariun roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

In an even most preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium venenatum* regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

Fungal cells may be transformed by a process involving protoplast formation, transformation of the protoplasts, and regeneration of the cell wall in a manner known per se. Suitable procedures for transformation of *Aspergillus host cells are described in EP* 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods For Obtaining Mutant Promoters

The present invention further relates to methods for obtaining a mutant promoter, comprising (a) introducing at least one mutation into the sequence of nucleotides 1 to 3949 of SEQ ID NO:1, nucleotides 1 to 938 of SEQ ID NO:2, or nucleotides 1 to 3060 of SEQ ID NO:3, wherein the mutant promoter has promoter activity; and (b) isolating the mutant promoter.

The present invention also relates to methods for obtaining a mutant promoter by (a) hybridizing a DNA under very low, low, medium, medium-high, high, or very high stringency conditions with (i) SEQ ID NO:1, SEQ ID NO:2, or SEQ ID NO:3, (ii) the cDNA sequence contained in SEQ ID NO:1, SEQ ID NO:2, or SEQ ID NO:3, (iii) a subsequence of (i) or (ii), or (iv) a complementary strand of (i), (ii), or (iii); and (b) isolating the mutant promoter from the DNA. Stringency and wash conditions are defined herein.

The mutant promoter may be isolated using methods known in the art such as restriction enzyme digestion or PCR amplification.

Nucleic Acid Sequences

The present invention also relates to isolated nucleic acid sequences, selected from the group consisting of:

(a) a nucleic acid sequence encoding a polypeptide having an amino acid sequence which has at least 65% identity with amino acids 22 to 581 of SEQ ID NO:4, at least 65% identity with amino acids 19 to 200 of SEQ ID NO:5, or at least 65% identity with amino acids 1 to 187 of SEQ ID NO:6;

(b) a nucleic acid sequence having at least 65% homology with nucleotides 4013 to 5743 of SEQ ID NO:1, at least 65% homology with nucleotides 993 to 1593 of SEQ ID NO:2, or at least 65% homology with nucleotides 3061 to 3678 of SEQ ID NO:3;

(c) a nucleic acid sequence which hybridizes under very low, low, medium, medium-high, high, or very high stringency conditions with (i) nucleotides 4013 to 5743 of SEQ ID NO:1, nucleotides 993 to 1593 of SEQ ID NO:2, or nucleotides 3061 to 3678 of SEQ ID NO:3; (ii) the cDNA sequence contained in nucleotides 4013 to 5743 of SEQ ID NO:1, nucleotides 993 to 1593 of SEQ ID NO:2, or nucleotides 3061 to 3678 of SEQ ID NO:3; (iii) a subsequence of (i) or (ii) of at least 100 nucleotides, or (iv) a complementary strand of (i), (ii), or (iii);

(d) a nucleic acid sequence encoding a variant of the polypeptide having an amino acid sequence of SEQ ID NO:4, SEQ ID. NO. 5, or SEQ ID NO:6 comprising a substitution, deletion, and/or insertion of one or more amino acids;

(e) an allelic variant of (a), (b), or (c); and (f) a subsequence of (a), (b), (c), or (e).

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

In a first embodiment, the present invention relates to isolated nucleic acid sequences encoding polypeptides having an amino acid sequence which has a degree of identity to amino acids 22 to 581 of SEQ ID NO:4, amino acids 19 to 200 of SEQ ID NO:5, or amino acids 1 to 187 of SEQ ID NO:6 (i.e., the mature polypeptide) of at least about 65%, preferably at least about 70%, more preferably at least about 80%, even more preferably at least about 90%, most preferably at least about 95%, and even most preferably at least about 97% (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 22 to 581 of SEQ ID NO:4, amino acids 19 to 200 of SEQ ID NO:5, or amino acids 1 to 187 of SEQ ID NO:6. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

Preferably, the nucleic acid sequences of the present invention encode polypeptides that comprise the amino acid sequence of SEQ ID NO:4, SEQ ID NO:5, or SEQ ID NO:6; or an allelic variant thereof; or a fragment thereof. In a more preferred embodiment, the nucleic acid sequence of the present invention encodes a polypeptide that comprises the amino acid sequence of SEQ ID NO:4, SEQ ID NO:5, or SEQ ID NO:6. In another preferred embodiment, the nucleic acid sequence of the present invention encodes a polypeptide that comprises amino acids 22 to 581 of SEQ ID NO:4, amino acids 19 to 200 of SEQ ID NO:5, or amino acids 1 to 187 of SEQ ID NO:6; or an allelic variant thereof; or a fragment thereof. In another preferred embodiment, the nucleic acid sequence of the present invention encodes a polypeptide that comprises amino acids 22 to 581 of SEQ ID NO:4, amino acids 19 to 200 of SEQ ID NO:5, or amino acids 1 to 187 of SEQ ID NO:6. In another preferred embodiment, the nucleic acid sequence of the present invention encodes a polypeptide that consists of the amino acid sequence of SEQ ID NO:4, SEQ ID NO:5, or SEQ ID NO:6; or an allelic variant thereof; or a fragment thereof. In another preferred embodiment, the nucleic acid sequence of the present invention encodes a polypeptide that consists of the amino acid sequence of SEQ ID NO:4, SEQ ID NO:5, or SEQ ID NO:6. In another preferred embodiment, the nucleic acid sequence of the present invention encodes a polypeptide that consists of amino acids 22 to 581 of SEQ ID NO:4, amino acids 19 to 200 of SEQ ID NO:5, or amino acids 1 to 187 of SEQ ID NO:6; or an allelic variant thereof; or a fragment thereof. In another preferred embodiment, the nucleic acid sequence of the present invention encodes a polypeptide that consists of amino acids 22 to 581 of SEQ ID NO:4, amino acids 19 to 200 of SEQ ID NO:5, or amino acids 1 to 187 of SEQ ID NO:6.

The present invention also encompasses nucleic acid sequences which encode a polypeptide having the amino acid sequence of SEQ ID NO:4, SEQ ID NO:5, or SEQ ID NO:6, which differ from SEQ ID NO:1, SEQ ID NO:2, or SEQ ID NO:3, respectively, by virtue of the degeneracy of the genetic code. The present invention also relates to subsequences of SEQ ID NO:1, SEQ ID NO:2, and SEQ ID NO:3 which encode fragments of SEQ ID NO:4, SEQ ID NO:5, and SEQ ID NO:6, respectively.

A subsequence is a nucleic acid sequence encompassed by SEQ ID NO:1, SEQ ID NO:2, or SEQ ID NO:3, except that one or more nucleotides from the 5' and/or 3' end have been deleted. Preferably, a subsequence of SEQ ID NO:1contains at least 1410 nucleotides, more preferably at least 1500 nucleotides, and most preferably at least 1590 nucleotides. Preferably, a subsequence of SEQ ID NO:2 contains at least 450 nucleotides, more preferably at least 480 nucleotides, and most preferably at least 510 nucleotides. Preferably, a subsequence of SEQ ID NO:3 contains at least 465 nucleotides, more preferably at least 495 nucleotides, and most preferably at least 525 nucleotides. A fragment of SEQ ID NO:4, SEQ ID NO:6, or SEQ ID NO:6 is a polypeptide having one or more amino acids deleted from the amino and/or carboxy terminus of this amino acid sequence. Preferably, a fragment of SEQ ID NO:4 contains at least 470 amino acid residues, more preferably at least 500 amino acid residues, and most preferably at least 530 amino acid residues. Preferably, a fragment of SEQ ID NO:5 contains at least 150 amino acid residues, more preferably at least 160 amino acid residues, and most preferably at least 170 amino acid residues. Preferably, a fragment of SEQ ID NO:6 contains at least 155 amino acid residues, more preferably at least 165 amino acid residues, and most preferably at least 175 amino acid residues.

An allelic variant denotes any of two or more alternative forms of a gene occupying the same chomosomal locus. Allelic variation arises naturally through mutation, and may result in polymorphism within populations. Gene mutations can be silent (no change in the encoded polypeptide) or may encode polypeptides having altered amino acid sequences. The allelic variant of a polypeptide is a polypeptide encoded by an allelic variant of a gene.

In a second embodiment, the present invention relates to isolated nucleic acid sequences which have a degree of homology to nucleotides 4013 to 5743 of SEQ ID NO:1, nucleotides 4013 to 1593 of SEQ ID NO:2, or nucleotides 3061 to 3678 of SEQ ID NO:3 (i.e., mature polypeptide coding region) of at least about 65%, preferably about 70%, preferably about 80%, more preferably about 90%, even more preferably about 95%, and most preferably about 97% homology, which encode an active polypeptide; or allelic variants and subsequences thereof. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

In a third embodiment, the present invention relates to isolated nucleic acid sequences encoding polypeptides which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 4013 to 5743 of SEQ ID NO:1, nucleotides 993 to 1593 of SEQ ID NO:2, or nucleotides 3061 to 3678 of SEQ ID NO:3; (ii) the cDNA sequence contained in nucleotides 4013 to 5743 of SEQ ID NO:1, nucleotides 993 to 1593 of SEQ ID NO:2, or nucleotides 3061 to 3678 of SEQ ID NO:3; (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y.). The subsequence of SEQ ID NO:1, SEQ ID NO:2, or SEQ ID NO:3 may be at least 100 nucleotides or preferably at least 200 nucleotides. Moreover, the subsequence may encode a polypeptide fragment.

The nucleic acid sequence of SEQ ID NO:1, SEQ ID NO:2, or SEQ ID NO:3, or a subsequence thereof, as well as the amino acid sequence of SEQ ID NO:4, SEQ ID NO:5, or SEQ ID NO:6, or a fragment thereof, may be used to design a nucleic acid probe to identify and clone DNA encoding polypeptides from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, SEQ ID NO:2, or SEQ ID NO:3, their complementary strands, or subsequences thereof, under very low to very high stringency conditions. Molecules to which the nucleic acid probe hybridizes under these conditions are detected using X-ray film.

In a preferred embodiment, the nucleic acid probe is the nucleic acid sequence of SEQ ID NO:1, SEQ ID NO:2, or SEQ ID NO:3. In another preferred embodiment, the nucleic acid probe is a nucleic acid sequence which encodes the polypeptide of SEQ ID NO:4, SEQ ID NO:5, or SEQ ID NO:6, or subsequences thereof. In another preferred embodiment, the nucleic acid probe is SEQ ID NO:1, SEQ ID NO:2, or SEQ ID NO:3. In another preferred embodiment, the nucleic acid probe is nucleotides 4013 to 5743 of SEQ ID NO:1, which encodes a mature polypeptide. In another preferred embodiment, the nucleic acid probe is nucleotides 993 to 5743 of SEQ ID NO:2, which encodes a mature polypeptide. In another preferred embodiment, the nucleic acid probe is nucleotides 3061 to 3678 of SEQ ID NO:3, which encodes a mature polypeptide. In another preferred embodiment, the nucleic acid probe is the nucleic acid sequence contained in plasmid pECO3 which is contained in *Escherichia coli* NRRL B-30067. In another preferred embodiment, the nucleic acid probe is the nucleic acid sequence contained in plasmid pFAMG which is contained in *Escherichia coli* NRRL B-30071. In another preferred embodiment, the nucleic acid probe is the nucleic acid sequence contained in plasmid pQUINN which is contained in *Escherichia coli* NRRL B-30076. In another preferred embodiment, the nucleic acid probe is the mature polypeptide coding region contained in plasmid pECO3 which is contained in *Escherichia coli* NRRL B-30067. In another preferred embodiment, the nucleic acid probe is the mature polypeptide coding region contained in plasmid pFAMG which is contained in *Escherichia coli* NRRL B-30071. In another preferred embodiment, the nucleic acid probe is the mature polypeptide coding region contained in plasmid pQUINN which is contained in *Escherichia coli* NRRL B-30076.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The present invention also relates to isolated nucleic acid sequences produced by (a) hybridizing a DNA under very low, low, medium, medium-high, high, or very high stringency conditions with (i) nucleotides 4013 to 5743 of SEQ ID NO:1, nucleotides 993 to 1593 of SEQ ID NO:2, or nucleotides 3061 to 3678 of SEQ ID NO:3, (ii) the cDNA sequence contained in nucleotides 4013 to 5743 of SEQ ID NO:1, nucleotides 993 to 1593 of SEQ ID NO:2, nucleotides 3061 to 3678 of SEQ ID NO:3, (iii) a subsequence of (i) or (ii), or (iv) a complementary strand of (i), (ii), or (iii); and (b) isolating the nucleic acid sequence from the DNA. The subsequence is preferably a sequence of at least 100 nucleotides such as a sequence which encodes a polypeptide fragment.

In a fourth embodiment, the present invention relates to isolated nucleic acid sequences which encode variants of the polypeptide having an amino acid sequence of SEQ ID NO:4, SEQ ID NO:5, or SEQ ID NO:6 comprising a substitution, deletion, and/or insertion of one or more amino acids.

The amino acid sequences of the variant polypeptides may differ from the amino acid sequence of SEQ ID NO:4, SEQ ID NO:5, or SEQ ID NO:6, or the mature polypeptides thereof, by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-bistidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins,* Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The nucleic acid sequences of the present invention may be obtained from microorganisms of any genus. For purposes of the present invention, the term "obtained from" is used as defined herein. In a preferred embodiment, the polypeptide encoded by a nucleic acid sequence of the present invention is secreted extracellularly.

The nucleic acid sequences may be obtained from a fungal source, and more preferably from a yeast strain such as a Candida, Hansenula, Kluyveromyces, Pichia, Saccharomyces, Schizosaccharomyces, or Yarrowia strain; or more preferably from a filamentous fungal strain such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Pironzyces, Schizophyllum, Talaroinyces, Thermoascus, Thielavia, Tolypocladium, or Trichoderma strain.

In a preferred embodiment, the nucleic acid sequences are obtained from a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* strain.

In another preferred embodiment, the nucleic acid sequences are obtained from an *Aspergillus aculeatus, Aspergillus awamori, Aspergillus foetidus, Aspergillus japonicus, Aspergillus nidulans, Aspergillus niger, Aspergillus oryzae, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* strain.

In another preferred embodiment, the nucleic acid sequences are obtained from a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum* strain.

In a more preferred embodiment, the nucleic acid sequences are obtained from *Fusarium venenatum,* and most preferably from *Fusariuin venenatum* ATCC 20334, e.g., the nucleic acid sequence set forth in SEQ ID NO:1, SEQ ID NO:2, or SEQ ID NO:3. In another more preferred embodiment, the nucleic acid sequence of SEQ ID NO:1 is the sequence contained in plasmid pECO3 which is contained in *Escherichia coli* NRRL B-30067. In another more preferred embodiment, the nucleic acid sequence of SEQ ID NO:2 is the sequence contained in plasmid pFAMG which is contained in *Escherichia coli* NRRL B-30071. In another more preferred embodiment, the nucleic acid sequence of SEQ ID NO:3 is the sequence contained in plasmid pQUINN which is contained in *Escherichia coli* NRRL B-300076. In another preferred embodiment, the nucleic acid sequence is nucleotides 4013 to 5743 of SEQ ID NO: 1, which encodes a mature polypeptide. In another preferred embodiment, the nucleic acid sequence is nucleotides 993 to 1593 of SEQ ID NO:2, which encodes a mature polypeptide. In another preferred embodiment, the nucleic acid sequence is nucleotides 3061 to 3678 of SEQ ID NO:3, which encodes a mature polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The present invention also relates to mutant nucleic acid sequences comprising at least one mutation in the mature polypeptide coding sequence of SEQ ID NO:1, SEQ ID NO:2, or SEQ ID NO:3, in which the mutant nucleic acid sequence encodes a polypeptide which consists of amino acids 22 to 581 of SEQ ID NO:4, amino acids 19 to 200 of SEQ ID NO:5, or amino acids 1 to 187 of SEQ ID NO:6, respectively.

The techniques used to isolate or clone a nucleic acid sequence encoding a polypeptide have been described herein.

The present invention also relates to nucleic acid constructs, recombinant vectors, and host cells containing the nucleic acid sequences described above. The same methods may be used as described earlier for their construction.

The present invention further relates to the polypeptides encoded by the nucleic acid sequences described above as well as methods of production of the polypeptides using the methods described herein.

The present invention is further described by the following examples which should not be construed as limiting the scope of the invention.

EXAMPLES

Chemicals used as buffers and substrates were commercial products of at least reagent grade.

Media and Solutions

COVE trace metals solution was composed per liter of 0.04 g of $NaB_4O_7$. $10H_2O$, 0.4 g of $CuSO_4$. $5H_2O$, 1.2 g of $FeSO_4$. $7H_2O$, 0.7 g of $MnSO_4$. $H_2O$, 0.8 g of $Na_2MoO_2$. $2H_2O$, and 10 g of $ZnSO_4$. $7H_2O$.

50×COVE salts solution was composed per liter of 26 g of KCl, 26 g of $MgSO_4$. $7H_2O$, 76 g of $KH_2PO_4$, and 50 ml of COVE trace metals.

COVE medium was composed per liter of 342.3 g of sucrose, 20 ml of 50×COVE salt solution, 10 ml of 1 M acetamide, 10 ml of 1.5 M $CsCl_2$, and 25 g of Noble agar.

50×Vogels medium was composed per liter of 150 g of sodium citrate, 250 g of $KH_2PO_4$, 10 g of $MgSO_4$. $7H_2O$, 10 g of $CaCl_2$. $2H_2O$, 2.5 ml of biotin stock solution, and 5.0 ml of AMG trace metals solution.

? Trace metals solution was composed per liter of 14.3 g of $ZnSO_4$. $7H_2O$, 2.5 g of $CuSO_4$. $5H_2O$, 0.5 g of $NiCl_2$, 13:8 g of $FeSO_4$, 8.5 g of $MnSO_4$, and 3.0 g of citric acid.

COVE top agarose was composed per liter of 20 ml of 50×COVE salts, 0.8 M sucrose, 1.5 M cesium chloride, 1.0 M acetamide, and 10 g of low melt agarose, pH adjusted to 6.0.

BASTA top agarose was composed of COVE top agarose supplemented with 10 mg/ml of the herbicide Basta™ (Hoechst Schering, Rodovre, Denmark).

RA sporulation medium was composed per liter of 50 g of succinic acid, 12.1 g of $NaNO_3$, 1 g of glucose, 20 ml of 50×Vogels, and 0.5 ml of a 10 mg/ml $NaMoO_4$ stock solution, pH to 6.0.

YEPG medium was composed per liter of 10 g of yeast extract, 20 g of peptone, and 20 g of glucose.

STC was composed of 0.8 M sorbitol, 25 mM Tris pH 8, 25 mM $CaCl_2$.

SPTC was composed of 40% PEG 4000, 0.8 M sorbitol, 25 mM Tris pH 8, 25 mM $CaCl_2$.

M400Da medium was composed per liter of 50 g of maltodextrin, 2 g of $MgSO_4$. $7H_2O$, 2 g of $KH_2PO_4$, 4 g of citric acid, 8 g of yeast extract, 2 g of urea, and 1 ml of COVE trace metals solution.

Example 1

Production of *Fusarium venenatum* Mycelial Tissue

*Fusarium venenatum CCl*-3, a morphological mutant of Fusarium strain ATCC 20334 (Wiebe et al., 1991, *Mycological Research* 95: 1284–1288), was grown in a two-liter lab-scale fermentor using a fed-batch fermentation scheme with NUTRIOSE™ (Roquette Freres, S.A., Beinheim, France) as the carbon source and yeast extract. Ammonium phosphate was provided in the feed. The pH was maintained at 6 to 6.5, and the temperature was kept at 30° C. with positive dissolved oxygen.

Mycelial samples were harvested at 2, 4, 6, and 8 days post-inoculum and quick-frozen in liquid nitrogen. The samples were stored at −80° C. until they were disrupted for RNA extraction.

Example 2 cDNA Library Construction

Total cellular RNA was extracted from the mycelial samples described in Example 1 according to the method of Timberlake and Barnard (1981, *Cell* 26: 29–37), and the RNA samples were analyzed by Northern hybridization after blotting from 1% formaldehyde-agarose gels (Davis et al., 1986, *Basic Methods in Molecular Biology,* Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 μg of poly(A)+mRNA according to the method of Gubler and Hoffman (1983, *Gene* 25: 263–269) except a NotI-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

The cDNA was digested with NotI, size selected by agarose gel electrophoresis (ca. 0.7–4.5 kb), and ligated with pZErO-2.1 (Invitrogen, Carlsbad, Calif.) which had been cleaved with NotI plus EcoRV and dephosphorylated with calf-intestine alkaline phosphatase (Boehringer Mannheim Corporation, Indianapolis, Ind.). The ligation mixture was used to transform competent *E. coli* TOPIO cells (Invitrogen, Carlsbad, Calif.). Transformants were selected on 2YT agar plates (Miller, 1992, *A Short Course in Bacterial Genetics. A Laboratory Manual and Handbook for Escherichia coli and Related Bacteria,* Cold Spring Harbor Press, Cold Spring Harbor, N.Y.) which contained kanamycin at a final concentration of 50 μg/ml.

Two independent directional cDNA libraries were constructed using the plasmid cloning vector pZErO-2.1. Library A was made using mRNA from mycelia harvested at four days, and Library B was constructed with mRNA from the six day time point. Neither cDNA library was amplified in order to examine a representative "snapshot" of the gene expression profile in the cells. Instead the libraries were plated, titered, and independent clones from each were analyzed by DNA sequencing.

Library A (4 day cells) consisted of about $7.5\times10^4$ independent clones and Library B (6 day cells) consisted of roughly $1.2\times10^5$ clones. Miniprep DNA was isolated from forty colonies in each library and checked for the presence and size of cDNA inserts. In this analysis 39 of 40 colonies (97.5%) from Library A contained inserts with sizes ranging from 600 bp to 2200 bp (avg.=1050 bp). Similarly, 39 of 40 colonies (97.5%) from Library B had inserts with sizes ranging from 800 bp to 3600 bp (avg.=1380 bp).

Example 3

Template Preparation and Nucleotide Sequencing

From each cDNA library described in Example 2, 1192 transformant colonies were picked directly from the transformation plates into 96-well microtiter dishes which contained 200 μl of 2YT broth (Miller, 1992, supra) with 50 μg/ml kanamycin. The plates were incubated overnight at 37° C. without shaking. After incubation 100 μl of sterile 50% glycerol were added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 μg of kanamycin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using the 96-well Miniprep Kit protocol of Advanced Genetic Technologies Corporation (Gaithersburg, Md.) as modified by Utterback et al. (1995, *Genome Sci. Technol.* 1: 1–8). Single-pass DNA sequencing was done with a Perkin-Elmer Applied Biosystems Model 377 XL Automatic DNA Sequencer (Perkin-Elmer Applied Biosystems, Inc., Foster City, Calif.) using dye-terminator chemistry (Giesecke et al., 1992, *Journal of Virology Methods* 38: 47–60) and the reverse lac sequencing primer.

Example 4

Analysis of DNA Sequence Data

Nucleotide sequence data were scrutinized for quality, and samples giving improper spacing less than or equal to 9.2 or ambiguity levels exceeding 3% were discarded or re-run. Vector sequences were trimmed with assistance of FACTURA™ software (Perkin-Elmer Applied Biosystems, Inc., Foster City, Calif.). In addition, sequences were truncated at the end of each sample when the number of ambiguous base calls increased. All sequences were compared to each other to construct overlapping contigs using TIGR Assembler software (Sutton, G. G. et al., 1995, *Genome Science and Technology* 1: 9019) to determine multiplicity of various cDNA species represented in each library. Lastly, all sequences were translated in three frames and searched against a non-redundant data base (NRDB) using GeneAssist™ software (Perkin-Elmer Applied Biosystems, Inc., Foster City, Calif.) with a modified Smith-Waterman algorithm using the BLOSUM 62 matrix with a threshold score of 70. The NRDB was assembled from Genpept, Swiss-Prot, and PIR databases.

Example 5

Identification of Glucoamylase cDNA Clones

Putative glucoamylase clones were identified by partial sequencing of random cDNA clones using an Applied Biosystems Model 377 XL Automated DNA Sequencer according to the manufacturer's instructions and comparison of the deduced amino acid sequence to the sequences in the NRDB as described in Example 4. From more than 2000 cDNA sequences analyzed, two clones from Library A and nine clones from Library B showed amino acid sequence homology to glucoamylase proteins from other fungi and yeasts. Among several glucoamylase cDNA clones discovered in this manner, one was estimated to be full-length (encoding the complete protein) on the basis of its alignment to the *Neurospora crassa* (Geneseq protein accession number R71034) and *Humicola grisea* (Trembi accession number Q12623) glucoamylase amino acid sequences and the presence of a possible signal peptide, detected using the Signal-P computer program (Nielsen, et al., 1997, *Protein Engineering* 10: 1–6). This clone designated *E. coli* FA0401 containing plasmid pFA0401 was selected for use as a probe to clone the corresponding glucoamylase genomic DNA sequence from *Fusarium venenatum* (see Example 7).

Example 6

Construction a Library of *Fusarium venenatum* Genomic DNA

Genomic libraries were constructed in λZipLox as specified by the procedure of Berka et al. (1998, *Appl. Environ. Microbiol.* 64, 4423–4427). Briefly, *Fusarium venenatum* total cellular DNA was partially digested with Tsp509I and size-fractionated on 1% agarose gels. DNA fragments migrating in the size range 3–7 kb were excised and eluted from the agarose gel slices using Prep-a-Gene reagents (BioRad, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified on *Escherichia coli* Y1090ZL cells and stored at 4° C. using standard methods (Davis, R. W., Botstein, D., and Roth, J. R., 1980, *Advanced Bacterial Genetics, A Manual for Genetic Engineering,* Cold Spring Harbor Press, Cold Spring Harbor, N.Y.).

Example 7

Isolation, Nucleotide Sequencing and Characterization of a Genomic DNA Segment Encoding *Fusarium venenatum* Glucoamylase Approximately 50,000 plaques from the *Fusarium venenatum* genomic DNA library (Example 6) were screened by hybridization (Davis et al., 1980, supra) with a radiolabeled probe fragment comprising the cloned cDNA insert from pFA0401 (Example 5) using high stringency conditions (i.e., hybridization at 45° C. in 50% formamide, 5×SSPE, 0.3% SDS, 200 μg/ml sheared and denatured salmon sperm DNA; filters washed once in 0.2×SSPE with 0.1% SDS at 45° C. followed by two washes in 0.2×SSPE with no SDS at the same temperature). Plaques which gave hybridization signals, were purified twice on *E. coli* Y1090ZL cells, and the individual clones were subsequently excised from the λZipLox vector as pZL1-derivatives (D'Alessio et al., 1992, *Focus®* 14: 76). DNA sequence analysis revealed that one of these clones, containing a plasmid designated pFAMG, comprised the entire glucoamylase coding region as well as 3.9 kb of 5'-flanking and 0.3 kb of 3'-flanking DNA encompassing the promoter and terminator regions, respectively (see FIG. 1).

DNA sequencing of the cloned insert in pFAMG was done with an Applied Biosystems Model 377 XL Automated DNA Sequencer using dye-terminator chemistry. Contiguous sequences were generated using a transposon insertion strategy (Primer Island Transposition Kit, Perkin-Elmer/Applied Biosystems, Inc., Foster City, Calif.), and the glucoamylase genomic clone from pFAMG was sequenced to an average redundancy of 4.2.

By comparing the genomic sequence data to the contig of glucoamylase cDNA sequences, it was determined that the genomic DNA segment encoding *Fusarium venenatum* glucoamylase contained an open reading frame of 1743 bp interrupted by an intron of 51 bp and encoding a polypeptide of 581 amino acids. The nucleotide sequence (SEQ ID NO:1) and deduced amino acid sequence (SEQ ID NO:4) are shown in FIG. 1. Using the SignalP program (Nielsen et al., 1997, *Protein Engineering* 10: 1–6), a signal peptide of 21 residues was predicted, and confirmed by amino terminal sequencing of the glucoamylase protein (Example 8). Thus, the mature glucoamylase is composed of 560 amino acids.

A comparative alignment of fungal glucoamylase protein sequences was undertaken using the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the *Fusarium venenatum* glucoamylase shares identity with the following glucoamylases from other fungi (percent identical residues in parentheses): *Neurospora crassa* [Swissprot P14804] (47%), *Aspergillus niger* [Swissprot P04064] (46%), *Humicola grisea* [Trembl Q12623] (44%), *Hormoconis resinae* [Swissprot Q03045] (41%), *Corticium rolfsii* [Q12596] (41%), *Schizosaccharomyces pombe* [Trembl 060087] (31%), and *Rhizopus oryzae* [Swissprot P07683] (23%).

Example 8

Amino Terminal Sequence Analysis of *Fusarium venenatum* Glucoamylase

The proteins in a sample of *Fusarium venenatum* fermentation broth (Example 1) were separated by 8–16% Tris-glycine SDS-PAGE (Novex, San Diego, Calif.) and electroblotted onto a PVDF membrane (Novex, San Diego, Calif.) using 10 mM CAPS (3-[cyclohexylamino]-1-propanesulfonic acid) in 10% methanol, pH=11.0 for 2 hours at 25 volts. The PVDF membrane was stained with 0.1% Commassie Blue R-250 in 40% methanol/1% acetic acid for 20 seconds and destained in 50% ethanol to observe the protein bands.

The major polypeptide species migrating at approximately 65 kDa was excised and subjected to N-terminal sequencing on an Applied Biosystems 476A Protein Sequencer (Perkin Elmer/Applied Biosystems Division, Foster City, Calif.) with on-line HPLC and liquid phase trifluoroacetic acid (TFA) delivery. Sequencing reagents were from Perkin Elmer/Applied Biosystems Division. (Foster City, Calif.). Detection of phenylthiohydantoin-amino acids was accomplished by on-line HPLC using Buffer A containing 3.5% tetrahydrofuran in water with 18 ml of the Premix concentrate (Perkin Elmer/Applied Biosystems Division, Foster City, Calif.) containing acetic acid, sodium acetate, and sodium hexanesulfonate and Buffer B containing Acetonitrile. Data was collected and analyzed on a Macintosh IIsi using Applied Biosystems 610 Data Analysis Software. Amino acid identifications were performed by visualizing chromatograms against a light source and determined by the operator. The N-terminal analysis yielded a protein sequence of Ser-Pro-Ser-Lys-Asp-Asn-Ser-Leu-Glu-Arg-Phe-Ile-Asp-Lys-Gln-Ala-Asp-Ile-Ser (SEQ ID NO:4).

Example 9

Identification of Abundant cDNA Clones Encoding an Putative Vacuolar Associated Protein and an Unknown Secreted Gene Product Two additional cDNA species were selected based on their relative abundance among the clones present in Libraries A and B (Example 2).

Clone FA0035, containing pFA0035, encoded a primary translation product of 200 amino acids with a possible signal peptide of 18 amino acids that was detected using the Signal-P computer program (Nielsen, et al., 1997, supra). Clone FA0035 was represented by approximately 1.9% of the cDNA clones in Library A and 0.8% of Library B. Comparison of the deduced amino acid sequence of clone FA0035 to the sequences in the NRDB as described in Example 4 revealed no significant homology to any known protein sequences, and it is therefore categorized as an unknown open reading frame (ORF). The name "Daria" was arbitrarily assigned to this clone.

Clone FA0759, containing plasmid pFA0759, encoded a polypeptide of 187 amino acids with 72% amino acid sequence identity to a putative subunit of the vacuolar associated protein from *Neurospora crassa* (Trembl accession number P87252). This gene product did not appear to be a secreted protein as no signal peptide was detected using Signal-P software. Clone FA0759 was represented by approximately 2.0% of the cDNA clones in Library A and 1.5% of Library B.

Example 10

Cloning and Nucleotide Sequence Analysis of Genomic DNA Segments Encoding Unknown Genes "Daria" and the Putative Vacuolar Associated Protein

*Fusarium venenatum* genomic DNA segments encoding the unknown secreted protein "Daria" and the putative vacuolar associated protein were isolated by screening the λZipLox library described in Examples 6 and 7. Radiolabeled cDNA inserts from plasmids pFA0035 and pFA0759 were used as probes to screen the library. Plaques which hybridized strongly to either probe using the same conditions in Example 7 were purified twice on *E. coli* Y1090ZL cells, and the individual clones were subsequently excised from the λZipLox vector as pZL1-derivatives (D'Alessio et al., 1992, supra).

DNA sequence analysis revealed that one of these clones, containing a plasmid designated as pECO3, comprised the entire "Daria" coding region as well as 0.9 kb of 5'-flanking and 0.9 kb of 3'-flanking DNA encompassing the promoter and terminator regions, respectively. The nucleotide sequence (SEQ ID NO:2) and deduced amino acid sequence (SEQ ID NO:5) are shown in FIG. 2. The coding region was punctuated by a single 55 bp intron.

Similarly, a genomic DNA clone was isolated through screening of the λZipLox library with a radiolabeled probe derived from the cDNA insert of pFA0579. The genomic clone, designated as pQUINN, encoded the entire vacuolar associated protein subunit plus 3.0 kb of 5'-flanking and 0.3 kb of 3'-flanking DNA comprising the promoter and terminator regions, respectively. The nucleotide sequence (SEQ ID NO:3) and deduced amino acid sequence (SEQ ID NO:6) are shown in FIG. 3. Nucleotide sequence comparisons between the genomic and cDNA clones revealed the presence of a 594 bp intron in the 5'-untranslated region of the putative vacuolar associated protein subunit. In addition, the coding region contained a 77 bp intron.

Example 11

Construction of pDMI81

Plasmid pDM181 was constructed using the technique of splice overlap extension to fuse the 1.2 kb *Fusarium oxysporum* trypsin promoter to the 1.1 kb *Fusarium oxysporum* trypsin terminator. A polylinker containing SwaI, KpnI and PacI restriction sites was inserted between the promoter and terminator as part of the overlapping PCR strategy. At the 5' end of the promoter a XhoI site was added and the native EcoRI site was preserved. At the 3' end of the terminator EcoRI, HindIII and NsiI sites were incorporated by the PCR reaction.

A PCR fragment containing −1208 to −1 of the *Fusarium oxysporum* trypsin promoter plus a 25 base pair polylinker was generated from plasmid pJRoy20(Royer et al., 1995, *Biotechnology* 13: 1479–1483) using the following primers:

```
Primer 1 (sense):       5'-GAGCTCGAGGAATTCTTACAAACCTTCAAC-3'            (SEQ ID NO:7)
                               XhoI   EcoRI

Primer 2 (antisense):   5'-TTAATTAAGGTACCTGAATTTAAATGGTGAAGAGATAGATATCCAAG-3'   (SEQ ID NO:8)
                             PacI    KpnI      SwaI
```

The 100 μl PCR reaction contained 10 ng of pJRoy20, 50 pmol of each primer, 1×Pwo buffer (Boehringer Mannheim, Indianapolis, Ind.), 200 μM each of dATP, dCTP, dGTP, and dTTP, and 5 units of Pwo DNA polymerase (Boehringer Mannheim, Indianapolis, Ind.). PCR conditions used were 95° C. for 3 minutes followed by 25 cycles at 95° C. for 30 seconds, 50° C. for 1 minute, and 72° C. for 1 minute. The final extension cycle was at 72° C. for 5 minutes.

Using the same PCR conditions, a second PCR fragment containing base pairs −5 to −1 of the *Fusariun oxysporum trypsin promoter, a* 25 base pair polylinker, and 1060 base pairs of the 3' untranslated region of the *Fusarium oxysporum* trypsin gene (terminator region) was generated from plasmid pJRoy2O using the following primers:

```
Primer 3 (sense):       5'-TCACCATTTAAATTCAGGTACCTTAATTAAATTCCTTGTTGGAAGCGTCGA-3'   (SEQ ID NO:9)
                                 SwaI      KpnI     PacI

Primer 4 (antisense):   5'-TGGTATGCATAAGCTTGAATTCAGGTAAACAAGATATAATTT-3'       (SEQ ID NO: 10)
                             NsiI HindIIIEcoRI
```

The final 2.3 kb overlapping PCR fragment which contained −1208 to −1 of the *Fusarium oxysporum* trypsin promoter, the 25 base pair polylinker and 1060 base pairs of the *Fusarium oxysporum* trypsin terminator was obtained using 0.2 μl of the first PCR (promoter) reaction and 3 μl of the second (terminator) reaction as templates and primers 1 and 4. The PCR conditions used were 95° C. for 3 minutes followed by 30 cycles at 95° C. for 30 seconds, 62° C. for 1 minute, and 72° C. for 3 minutes. The final extension cycle was at 72° C. for 5 minutes. Pwo DNA polymerase was also used for this reaction.

The resulting 2.3 kb fragment containing the trypsin promoter, the polylinker, and the trypsin terminator was digested with EcoRI and ligated into the EcoRI digested vector pMT1612 containing the bar gene (WO 97/26330) to create pDM181 (FIG. 4).

Example 12

Construction of plasmid pSheB1

Figure 5:
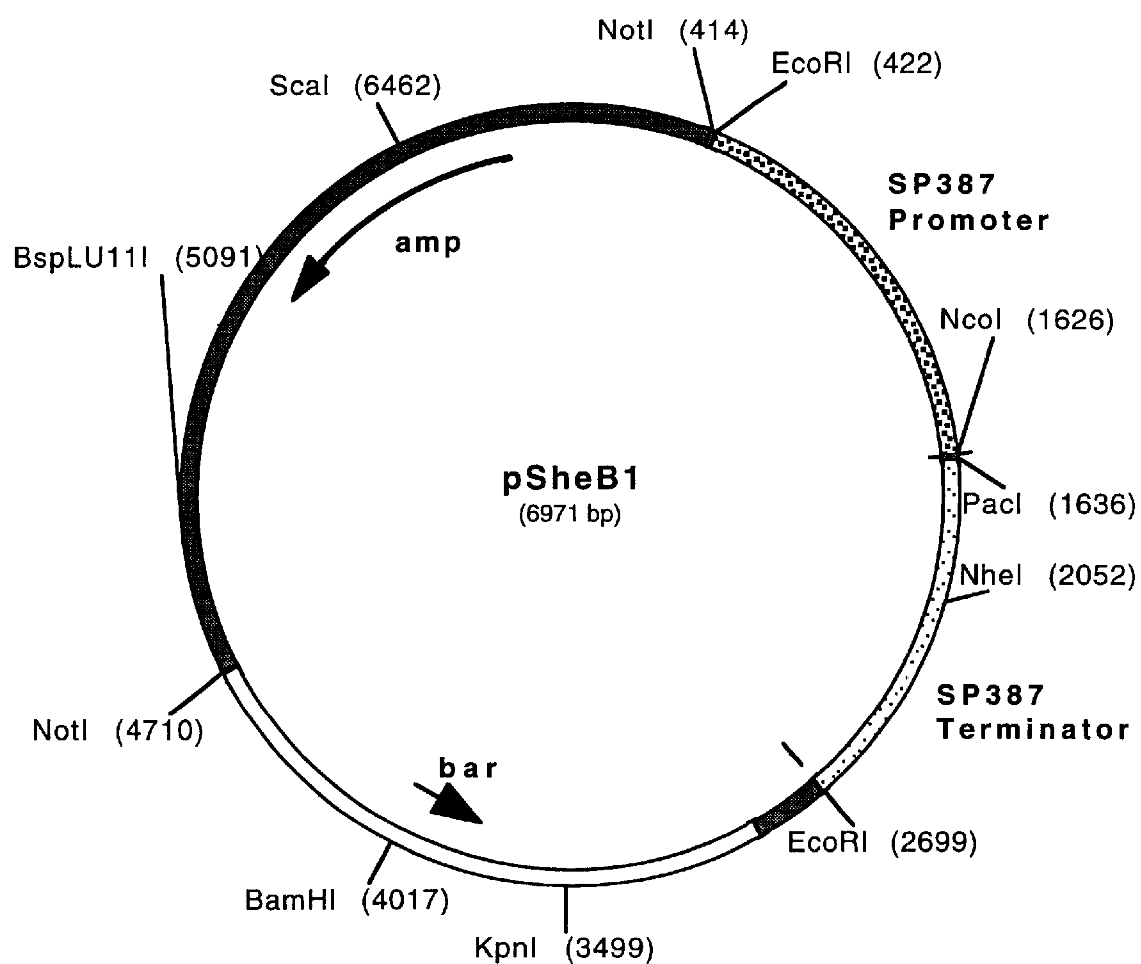
FIG. 5 shows a restriction map of pSheB1.

The *Fusarium venenatum* expression vector pSheB1 (FIG. 5) was generated by modification of pDM181. The modifications included (a) removal of two NcoI sites within the pDM181 sequence, and (b) restoration of the natural translation start of the *Fusarium oxysporum* trypsin promoter (reconstruction of an NcoI site at the ATG start codon).

Removal of two NcoI sites within the pDM181 sequence was accomplished using the QuikChange™ site-directed mutagenesis kit (Stratagene Cloning Systems, La Jolla, Calif.) according to the manufacturer's instruction with the following pairs of mutagenesis primers:

5'-dCAGTGAATTGGCCTCGATGGCCGCGGCCGCGAATT-3' plus (SEQ ID NO:11)

5'-dAATTCGCGGCCGCGGCCATCGAGGCCAATTCACTG-3' (SEQ ID NO:12)

5'-dCACGAAGGAAAGACGATGGCTTTCACGGTGTCTG-3' plus (SEQ ID NO:13)

5'-dCAGACACCGTGAAAGCCATCGTCTTTCCTTCGTG-3' (SEQ ID NO:14)

Restoration of the natural translation start of the *Fusarium oxysporum* trypsin promoter was also accomplished using the Stratagene QuikChange™ site directed mutagenesis kit in conjunction with the following pair of mutagenesis primers:

5'-dCTATCTCTTCACCATGGTACCTTAATTAAATACCTTGTTGGAAGCG-3' plus (SEQ ID NO:15)

5'-dCGCTTCCAACAAGGTATTTAATTAAGGTACCATGGTGAAGAGATAG-3' (SEQ ID NO:16)

All site-directed changes were confirmed by DNA sequence analysis of the appropriate vector regions.

Example 13

Construction of pDM194 and pDM218

The 7.8 kb plasmid pDM194 (7.8 kb) used to obtain expression of *Thermomyces lanuginosus* (formerly designated *Humicola lanuginosa* ) lipase in *Fusarium venenatum* has the following gene elements:

A 1.2 kb DNA segment containing the *Fusarium oxysporum* trypsin gene promoter (Royer et al., 1995, supra).

A 0.9 kb DNA fragment containing the *Thermomyces lanuginosus* lipase cDNA (EP 305 216).

A 1.1 kb DNA segment containing the *Fusarium oxysporum* trypsin gene terminator (Royer et al., 1995, supra).

A 4.7 kb fragment of DNA from pMTI612 (WO 98/11203) containing the 2.8 kb *E. coli* vector pUC19 and a 1.8 kB fragment comprising the *Aspergillus nidulans* amdS gene promoter (Hynes et al., 1988, *Mol. Cell. Biol.* 8: 2589–2596), *Streptomyces hygroscopicus* phosphinothricin acetyltransferase (bar) gene (Thompson et al., 1987, *EMBO Journal* 6: 2519–2514), and *Aspergillus niger* AMG terminator.

The SwaI/PacI lipase fragment was generated by PCR. Plasmid pMHan37 which contains the cDNA of the *Thermomyces lanuginosus* lipase gene (EP 305 216) was used as the template. PCR primers 5 and 6 shown below were used to introduce a SwaI site at the 5' end and a PacI site at the 3' end of the lipase coding region.

```
Primer 5 (sense):                         (SEQ ID NO: 17)
        5'-ATTTAAATGATGAGGAGCTCCCTTGTGCTG-3'
           SwaI

Primer 6 (anti-sense):                    (SEQ ID NO: 18)
        5'-TTAATTAACTAGAGTCGACCCAGCCGCGC-3'
           PacI
```

Figure 6:
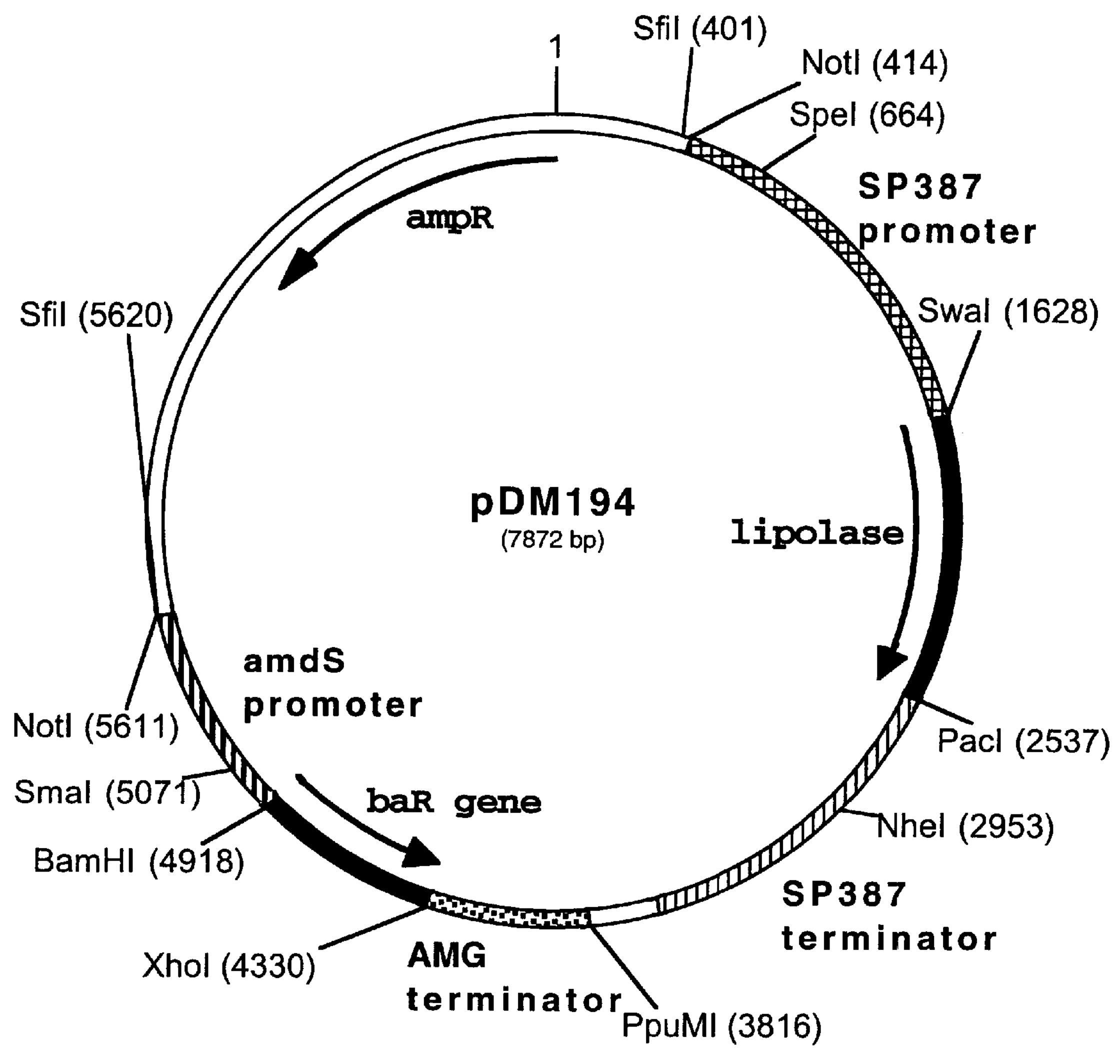
FIG. 6 shows a restriction map of pDM194.
Figure 7:
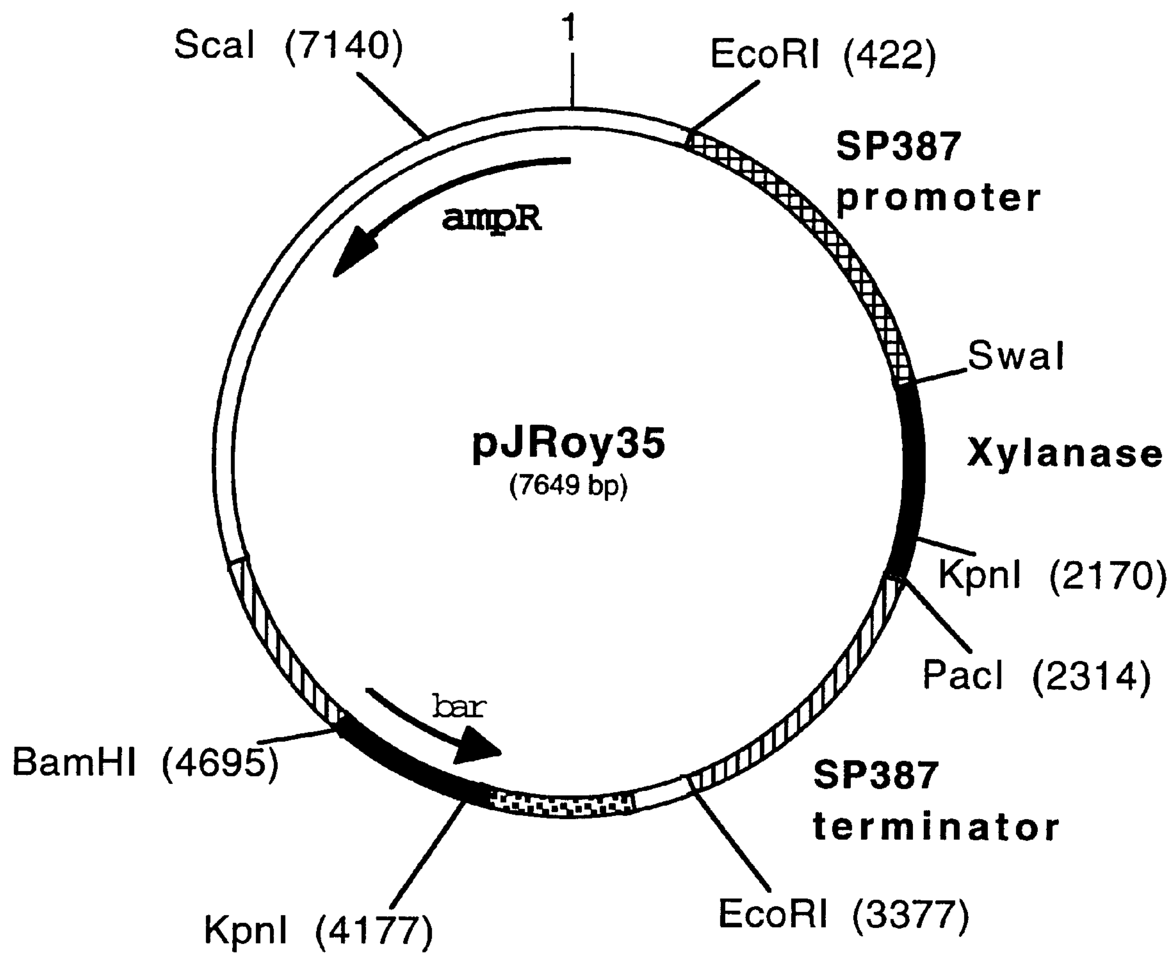
FIG. 7 shows a restriction map of pJRoy35.

The 100 μl PCR reaction contained 10 ng of pMHan37, 50 pmol of each primer, 1×PCR buffer (Perkin-Elmer Corp., Branchburg, N.J.), 250 μM each of dATP, dCTP, dGTP, and dTTP, and 5 units of Taq DNA polymerase (Perkin-Elmer Corp., Branchburg, N.J.). The PCR conditions used were one cycle at 95° C. for five minutes followed by 30 cycles at 95° C. for 1 minute, 55° C. for one minute, and 72° C. for two minutes. The 0.9 kb PCR product was subcloned into pCRII of the TA Cloning Kit (Invitrogen, Carlsbad, Calif.) according to the manufacturer's instructions. Plasmid DNA was isolated using a Qiagen Maxiprep Kit (Qiagen, Santa Clarita, Calif.), digested with SwaI and PacI, and electrophoresed on a 1% agarose gel for one hour at 100 volts. The 0.9 kb fragment was excised, purified using a SpinBind Kit (FMC, Rockland, Me.), and cloned into pBANe6 (WO 98/11203) to produce pBANe8.

pBANe8 was digested with SwaI and PacI and the 0.9 kb lipase fragment was ligated to SwaI/PacI digested pDM 181 yielding lipase expression plasmid pDM 194 (FIG. 6). pDM218 was constructed from pJRoy35 (FIG. 7). NotI and PmeI restriction sites were introduced at the 5' end of the *Fusarium oxysporum* trypsin promoter by PCR. A 362 bp amplicon containing the 5' end of the promoter was produced using pDM194 as a template with the following primers:

multi1: 5'-ATAAGAATGCGGCCGCTAGTTTAAACTTACAAACCTTCAACAGTG-3' (SEQ ID NO:19)

multi 2: 5'-TAGCATCTATCTCCGTCTT-3' (SEQ ID NO:20)

The 100 μl PCR reaction contained 150 ng of 3 kb EcoRI fragment, 50 pmol of each primer, 1×Pwo buffer, 200 μM each of dATP, dCTP, dGTP, and dTTP, and 5 units of Pwo DNA polymerase. The PCR conditions used were one cycle at 95° C. for 3 minutes, 30 cycles at 95° C. for 1 minute, 50° C. for 1 minute, and 72° C. for 1.5 minutes; followed by a 5 minute extension at 72° C. The amplicon was subcloned into vector pCR-Blunt (Invitrogen, Carlsbad, Calif.). A 0.25 kb NotI/BcuI fragment was electrophoresed on a 1% agarose gel for one hour at 100 volts, excised, and purified using a QIAquick Gel Extraction Kit (Qiagen, Santa Clarita, Calif.).

HpaI, SnaBI, and PpuMI sites were introduced at the 3' end of the *Fusarium oxysporum* trypsin terminator by PCR. A 714 bp amplicon containing the 3' end of the trypsin terminator was produced using the 3 kb EcoRI fragment as template with the following primers:

multi3: 5'-GTGTGCAGTGACCCAGAAT-3' (SEQ ID NO:21)

multi4: 5'-GATTGGGTCCCTACGTAGTTAACACTATAGGCCATCGTTTAC-3' (SEQ ID NO:22)

The 100 μl PCR reaction contained 50 pmol of each primer, 150 ng of the 3 kb EcoRI fragment, 1×Pwo buffer, 200 μM each of dATP, dCTP, dGTP, and dTTP, and 5 units of Pwo DNA polymerase. The PCR conditions used were identical to those listed above. The amplicon was subcloned into vector pCR-Blunt. A 0.62 kb NheI/PpuMI fragment was isolated as described above.

A 2.3 kb BcuI/NheI fragment containing the 3' end of the *Fusarium oxysporum* trypsin promoter, the *Humicola lanuginosa* lipase gene (Geneseq nucleotide accession number N91076), and the 5' end of the *Fusarium oxysporum* trypsin terminator was isolated from pDMI94.

Figure 8:
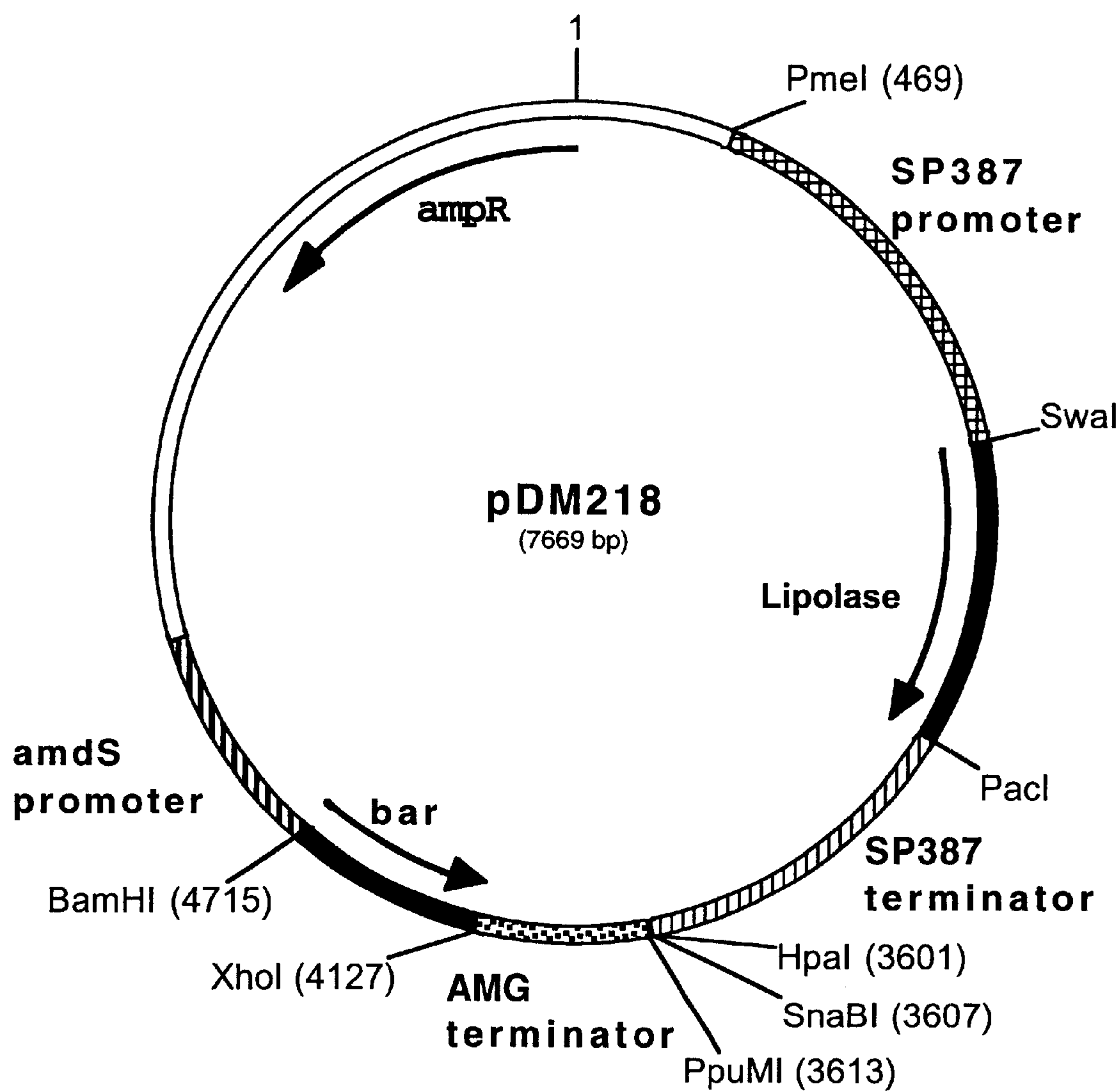
FIG. 8 shows a restriction map of pDM218.

The 0.25 kb NotI/BcuI fragment, 2.3 kb BcuI/NheI fragment, and 0.62 kb NheI/PpuMI fragments were cloned together into pDMI94 partially digested with NotI and completely digested with PpuMI to create pDM218 (FIG. 8).

Example 14

Construction of Plasmid pMWR60

The plasmid pMWR60 was derived from the expression vector pEJG25A. pEJG25A was constructed by insertion of a phytase coding sequence from *Peniophora lycii* (WO 98/28408) into pDM181 (Example 11) as follows:

First, two synthetic oligonucleotide primers shown below were designed to amplify the *Peniophora lyci* phytase coding sequence from plasmid pAlphy2 (WO 98/28408) as template by PCR.

Forward primer: 5'-ATTTAAATATGGTTTCTTCGGCATTCGC-3' (SEQ ID NO:23)

Reverse primer: 5'-TTAATTAACTATTCCGACGGAACAAAGC-3' (SEQ ID NO:24)

(Bold letters represent coding sequence).

Figure 9:
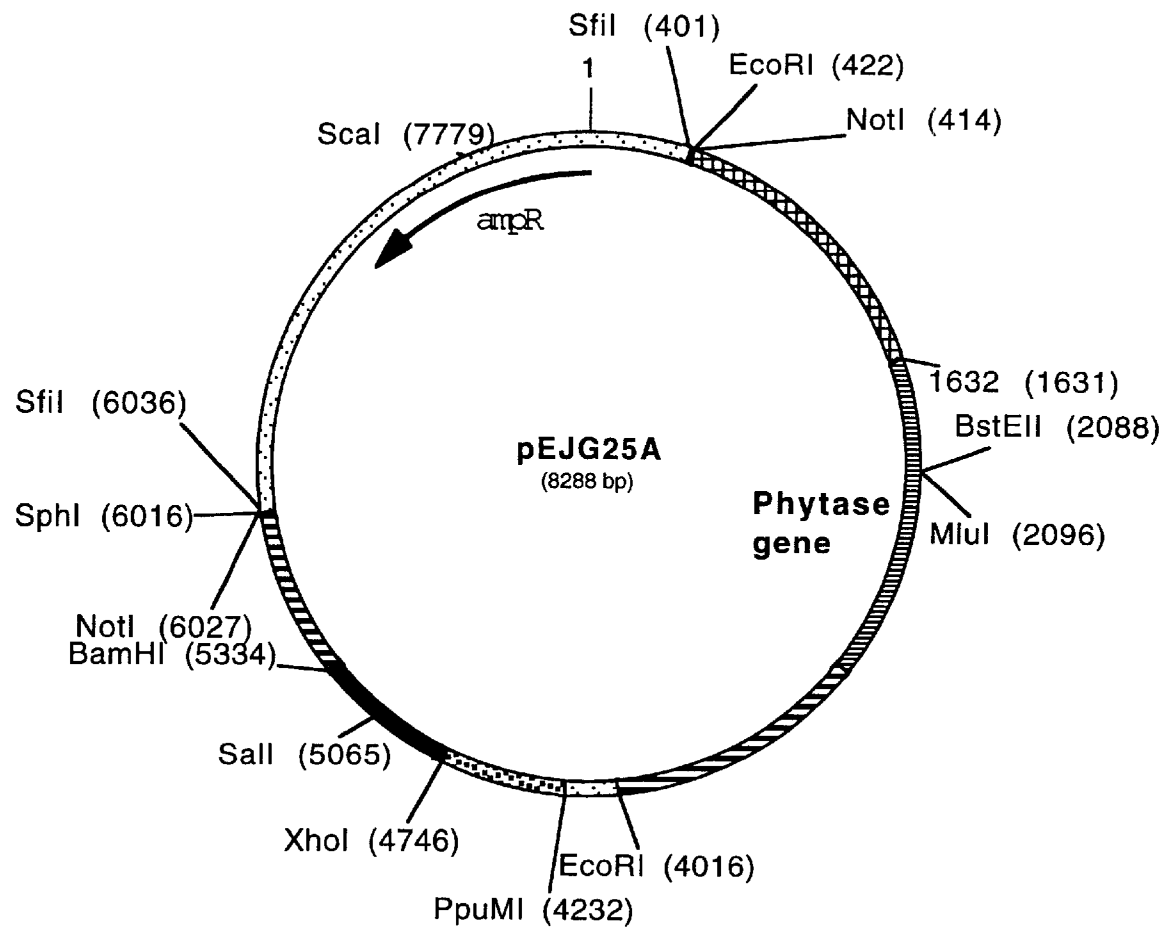
FIG. 9 shows a restriction map of pEJG25A.

Each 100 μl Pwo polymerase reaction contained 50 pmol of each primer, 1 ng of template DNA, 2 μl of 10 mM dNTPs, 1×Pwo polymerase buffer, and 2.5 units of Pwo polymerase. The reactions were incubated in a Perkin Elmer Model 9600 Thermal Cycler programmed as follows: One cycle at 94° C. for 2 minutes, 55° C. for 30 seconds, and 72° C. for 1 minute; 9 cycles at 94° C. for 15 seconds, 55° C. for 30 seconds, and 72° C. for 1 minute; 15 cycles at 94° C. for 15 seconds, 55° C. for 30 seconds, and 72° C. for 1 minute, with an extension of 20 seconds per cycle; a final cycle at 94° C. for 15 seconds, 55° C. for 30 seconds, and 72° C. for 7 minutes; and a soak cycle at 4° C. The reaction product was electrophoresed on a 1% agarose gel for one hour at 100 volts. The 1.3 kb band was excised and purified using Qiaex II. The purified PCR product was subsequently cloned into the plasmid pCR2. 1 (Invitrogen, Carlsbad, Calif.) and used to transform *E. coli* TOP10 cells (Invitrogen, Carlsbad, Calif.). Plasmid DNA was isolated from several of the transformant colonies and analyzed by DNA sequencing to ensure that no mutations were introduced during the PCR. Subsequently one phytase clone was digested with restriction endonucleases SwaI and PacI. The fragments were electrophoresed on a 1% agarose gel for one hour at 100 volts, excised, and purified using Qiaex II. The 1.3 kb phytase gene fragment was ligated with pDM181 (Example 11) that had been previously cut with SwaI and PacI, resulting in the expression plasmid pEJG25A (FIG. 9).

In order to remove extraneous linker sequences in the 5'-flanking DNA, pEJG25A was mutagenized using the Quick-Change™ site-directed mutagenesis kit in combination with the following oligonucleotide primers to obtain the vector pMWR60-Int2:

primer A: 5'-CTCTTGGATATCTATCTCTTCACCATGGTTTCTTCGGCATTCGC-3' (SEQ ID NO:25)

primer B: 5'-GCGAATGCCGAAGAAACCATGGTGAAGAGTAGATATCCAAGAG-3' (SEQ ID NO:26)

Figure 10:
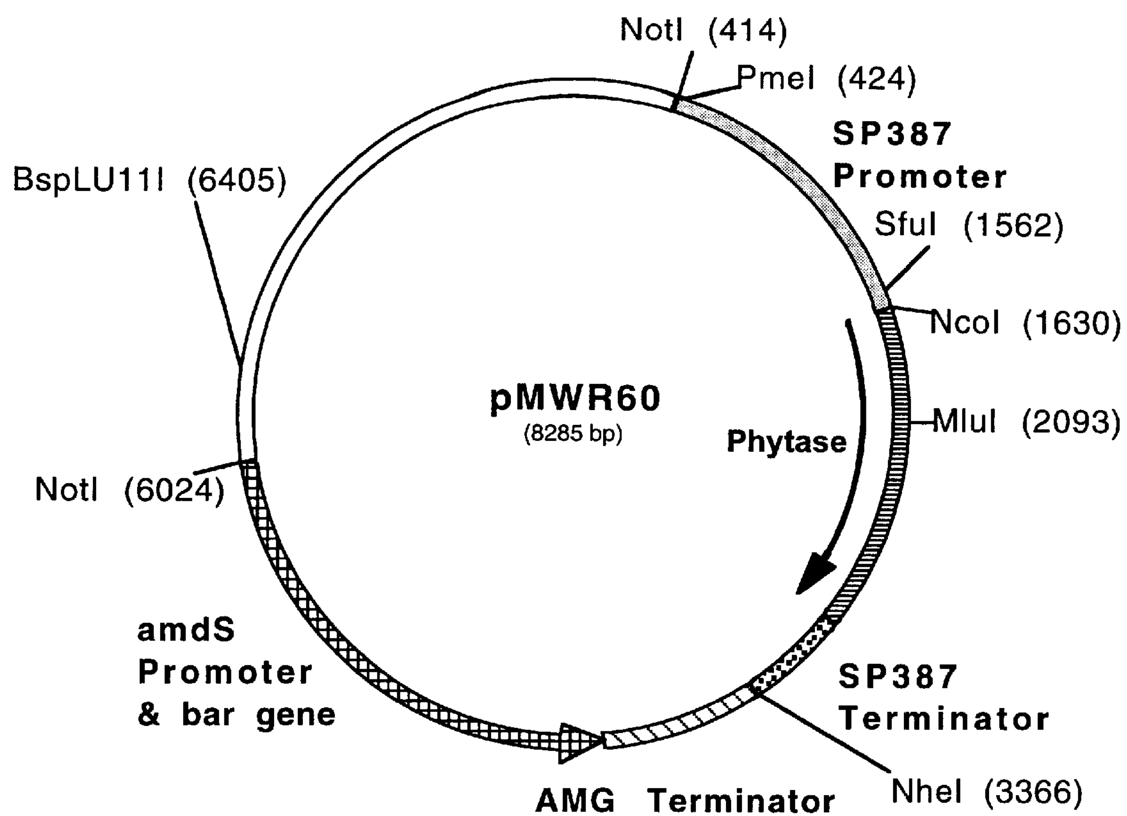
FIG. 10 shows a restriction map of pMWR60.

The designed nucleotide changes were verified by DNA sequence analysis.

pMWR60-Int2 was then digested with SfuI plus NheI, and the 1.8 kb fragment was electrophoresed on a 1% agarose gel for one hour at 100 volts, excised, and purified using Qiaex II. The isolated fragment was ligated with the SfuI-NheI vector fragment of pDM218 to generate a new intermediate called pMWR60-Int3. This intermediate was cleaved with NotI, and a 5.35 kb fragment was purified as above. The purified fragment was ligated with pSheB1 (described in Example 12) which had been previously digested with NotI. The resulting intermediate was designated as pMWR60-Int4a. pMWR60-Int4a was then cut with BspLU11I plus NheI, and a 5.25 kb segment was purified as above. This isolated segment was ligated with pSheB1, which had also been digested with BspLU11I plus NheI, and purified as above. The resulting vector product was named pMWR60 (FIG. 10).

Example 15

Generation of a Lipase Reporter Gene

For the construction of variants of a *Humicola lanuginosa* lipase known as LIPOLASE™ (Novo Nordisk A/S, Bagsvaerd, Denmark), the Chameleon double-stranded, site-directed mutagenesis kit was used according to the manufacturer's instructions.

The gene encoding the LIPOLASE™ enzyme was obtained from pAHL (WO 92/05249). In accordance with the manufacturer's instructions, the ScaI site of the ampicillin gene of pAHL was changed to a MluI site by use of the primer 7258, thus changing the ScaI site found in the ampicillin resistance gene and used for cutting to a MluI site. Primer 7258: 5'-GAATGACTTGGTTGACGCGTCACCAGTCAC-3' (SEQ ID NO:27)

The pAHL vector comprising the LIPOLASE™ gene was then used as a template for DNA polymerase with oligos 7258 and 7770, thus changing the ScaI site found in the LIPOLASE™ gene and without changing the amino acid sequence site. Primer 7770: 5'-TCTAGCCCAGAATACTGGATCAAATC-3' (SEQ ID NO:28)

The desired mutation (e.g., the introduction of a cysteine residue) was introduced into the LIPOLASE™ gene by addition of an appropriate oligos comprising the desired mutation.

Site directed mutagenesis as described above was used to construct a plasmid harboring a gene encoding the LIPOLASE™ variant IS, E239C, Q249R using the following primers:

Primer 106659 shown below was used to introduce E99N, N101S.

Primer 107581:
5'-CTTAACTTTGACTTGAAAAACATATCTGACATTTGCTCC-3' (SEQ ID NO:29)

Primer 101782 shown below was used to introduce SPPCGRRP (-E).

Primer 101782:
5'-GGACGGCCTTGGCTAGCCCTCCGTGCGGCCGCCGGCCGGTCTCGCAGGATCTGT TTAAC-3' (SEQ ID NO:30)

Primer 9639 shown below was used to introduce E239C.

Primer 9639: 5'-ATATCGTGAAGATATGCGGCATTGATGCCACC-3' (SEQ ID NO:31)

Primer 8829 shown below was used to introduce Q249R.

Primer 8829: 5'-GGCGGCAATAACCGGCCGAACATTC CGGATATCCC-3' (SEQ ID NO:32)

The mutations were verified by sequencing the entire gene. The resulting plasmid was designated pEVi1163.

Example 16

Construction of pRaMB60

Plasmid pRaMB60 was constructed by ligating the 6.5 kb SfuI-NheI vector fragment from pMWR60 with a 0.5 kb SfuI-NheI fragment from pSheB1. All fragments were isolated by agarose gel electrophoresis and purified from gel slices using BioRad Prep-a-Gene reagents (BioRad Laboratories, Hercules, Calif.).

Example 17

Construction of Plasmid pRaMB62, an Expression Vector Containing the Glucoamylase Promoter A unique BspLU11I site was generated by site-directed mutagenesis of plasmid pFAMG using the following primers in combination with the Quick-Change™ mutagenesis kit:

primer 1: 5'-dCACTGCTATCACCAACATGTTTAC TCAAGTCC-3' (SEQ ID NO:33)

primer 2: 5'-dGGACTTGAGTAAACATGTTGGTG ATAGCAGTG-3' (SEQ ID NO:34)

The site-directed change was verified by DNA sequencing, and the resulting plasmid derivative was designated pMWR62-Intl.

Next, the lipase reporter gene described in Example 15 was amplified by PCR using plasmid pEVi 1163 as template with the following primers which introduced a BspHI site near the start codon and a PacI site following the stop codon of the lipase coding region:

forward primer: 5'-GACTCATGAGGAGCTCCCTTG TGCTGTTC-3' (SEQ ID NO:35)

reverse primer: 5'-TGATTAATTAACCTAAAGACATGT CCCAATTAAC-3' (SEQ ID NO:36)

The PCR reaction was composed of 1 μl of template DNA (10 ng), 1 μl of forward primer (77 pmol), 1 μl of reverse primer (81 pmol), 10 μl of 10×Pwo polymerase buffer, 16 μl of 1.25 mM dNTP mix, and 1 μl (2.5 units) of Pwo polymerase. The reaction was incubated in a Perkin-Elmer Model 480 thermocycler using the following temperature settings: One cycle at 95° C. for 5 minutes; 30 cycles at 95° C. for 1 minute, 47° C. for 1 minute, and 68° C. for 2 minutes; and a 4° C. soak cycle.

Figure 11:
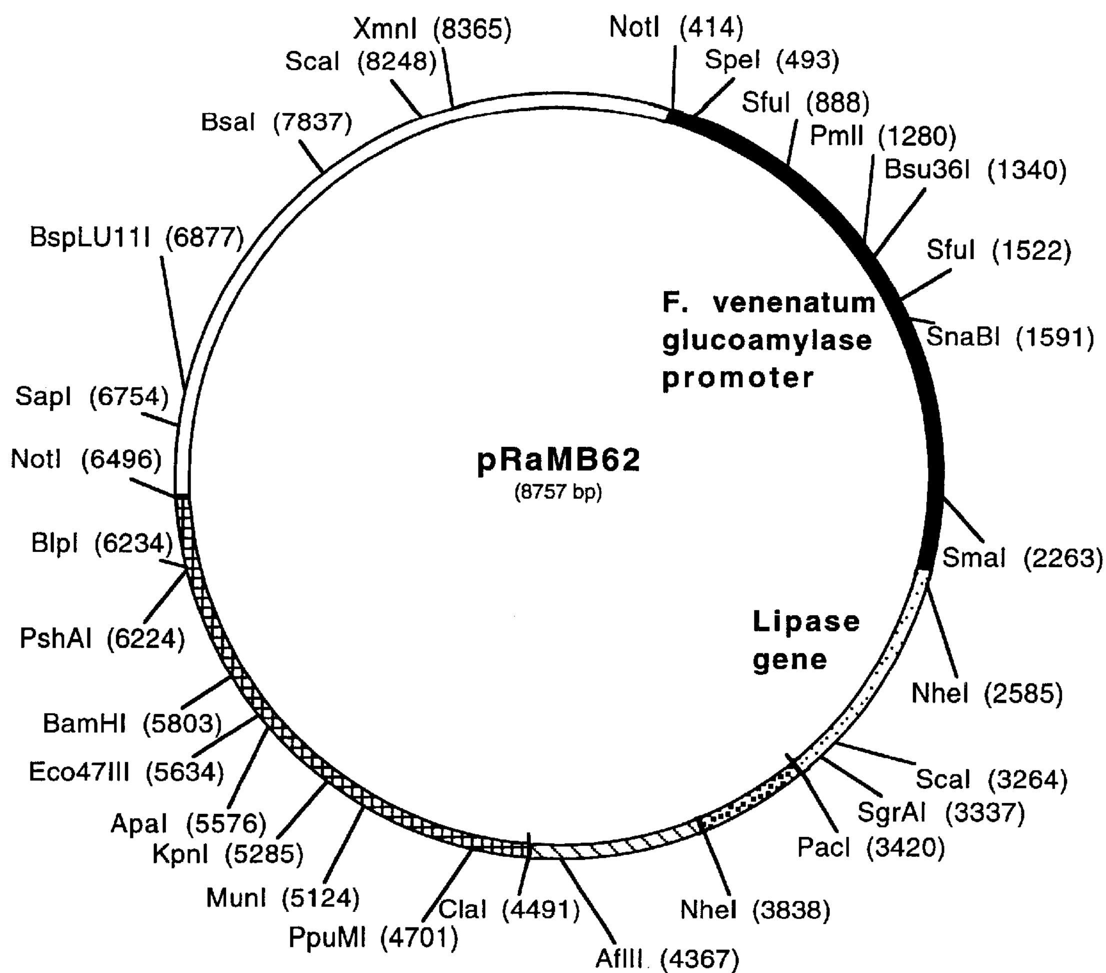
FIG. 11 shows a restriction map of pRaMB62.

The amplified product was then digested with BspHI plus PacI, purified by agarose gel electrophoresis (Example 16), and used in a three-part ligation with the 5.8 kb PmeI-NcoI fragment of pRaMB60 and the 2.1 kb StuI-BspLU11I fragment from pMWR62-intl. The resulting vector, designated pRaMB62 (FIG. 11), contained the lipase reporter gene under the transcriptional control of the *Fusarium venenatum* glucoamylase promoter.

Example 18

Construction of Plasmid pRaMB64, an Expression Vector Containing the "Daria" Promoter The promoter region from pEC03 (Example 10), termed the "Daria" promoter, was amplified using PCR in combination with the following primer pair that were designed to introduce SwaI and BspLU11 I sites at the 5' and 3' ends of the promoter segment, respectively:

primer 1: 5'-GCATTTAAATTACTACTGTGATGTG-3' (SEQ ID NO:37)

primer 2: 5'-GATTGATGTGAAACACATGTTGATG-3' (SEQ ID NO:38)

The PCR reaction was composed of 1 μl of pECO3 (10 ng), 1 μl of forward primer (50 pmol), 1 μl of reverse primer (50 pmol), 10 μl of 10×Pwo polymerase buffer, 16 μl of 1.25 mM dNTP mix, and 1 μl (2.5 units) of Pwo polymerase. The reaction was incubated in a Perkin-Elmer Model 480 thermocycler using the following temperature settings: One cycle at 95° C. for 5 minutes; 30 cycles at 95° C. for 1 minute, 47° C. for 1 minute, and 68° C. for 2 minutes; and a 4° C. soak cycle.

The 0.9 kb PCR product was electrophoresed on a 1% agarose gel for one hour at 100 volts, excised, and purified using Qiaex II.

Figure 12:
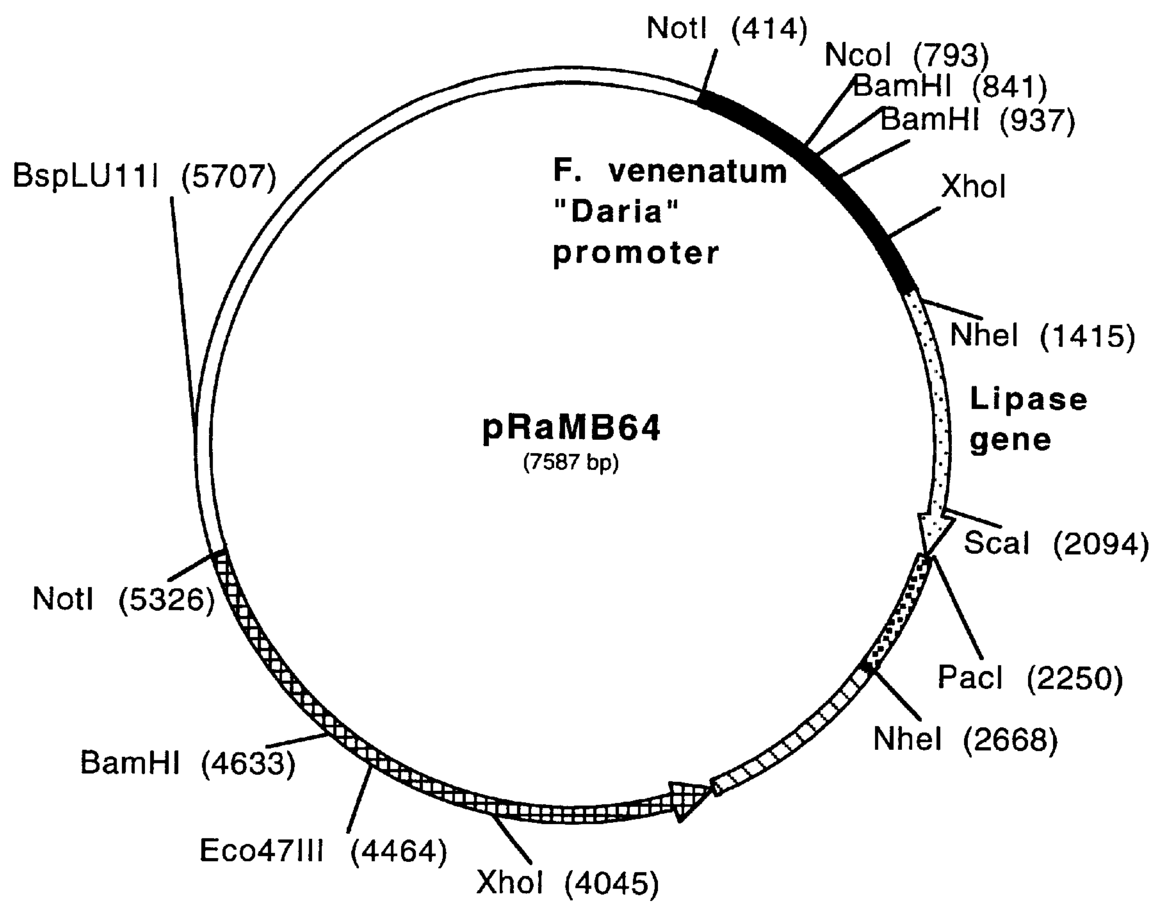
FIG. 12 shows a restriction map of pRaMB64.

The amplified DNA segment was subcloned into pCR2.1 (Invitrogen, Carlsbad, Calif.) and analyzed by restriction enzyme cleavage with SwaI, BspLU11I, EcoRI, and XhoI to verify that it was correct. The plasmid generated in this manner, termed pECO4, was digested with SwaI plus BspLU11I, and the 0.9 kb promoter fragment was purified by gel electrophoresis as described in Example 16. The purified fragment was mixed in a three-part ligation with the 5.8 kb PmeI-NcoI fragment of pRaMB60 and the 0.9 kb BspHI-PacI segment encoding the lipase reporter gene. The product of this ligation, pRaMB64 (FIG. 12), contained the "Daria" promoter directing expression of the lipase reporter gene.

Example 19

Construction of Plasmid pRaMB66, an Expression Vector Containing the Promoter Derived from the Vacuolar Associated Protein Gene The promoter segment from pQUINN (Example 10), encoding a putative vacuolar associated protein, was amplified by PCR with the following primers which introduced a SmaI site and an NcoI site at the 5' and 3' ends of the promoter, respectively:

primer 1: 5'-dCGACCCGGGAATTAGAGAGGTTAGG-3' (SEQ ID NO:39)

primer 2: 5'-dCGTATAACCCATGGTGGACTTG TCGGAC-3' (SEQ ID NO:40)

The PCR reaction was composed of 1 μl of pQUNN (10 ng), 1 μl of forward primer (50 pmol), 1 μl of reverse primer (50 pmol), 10 μl of 10×Pwo polymerase buffer, 16 μl of 1.25 mM dNTP mix, and 1 μl (2.5 units) of Pwo polymerase. The reaction was incubated in a Perkin-Elmer Model 480 thermocycler using the following temperature settings: One cycle at 95° C. for 5 minutes; 30 cycles at 95° C. for 1 minute, 47° C. for 1 minute, and 68° C. for 2 minutes; and a 4° C. soak cycle.

The 3.1 kb amplified DNA fragment was electrophoresed on a 1% agarose gel for one hour at 100 volts, excised, and purified using Qiaex II.

Figure 13:
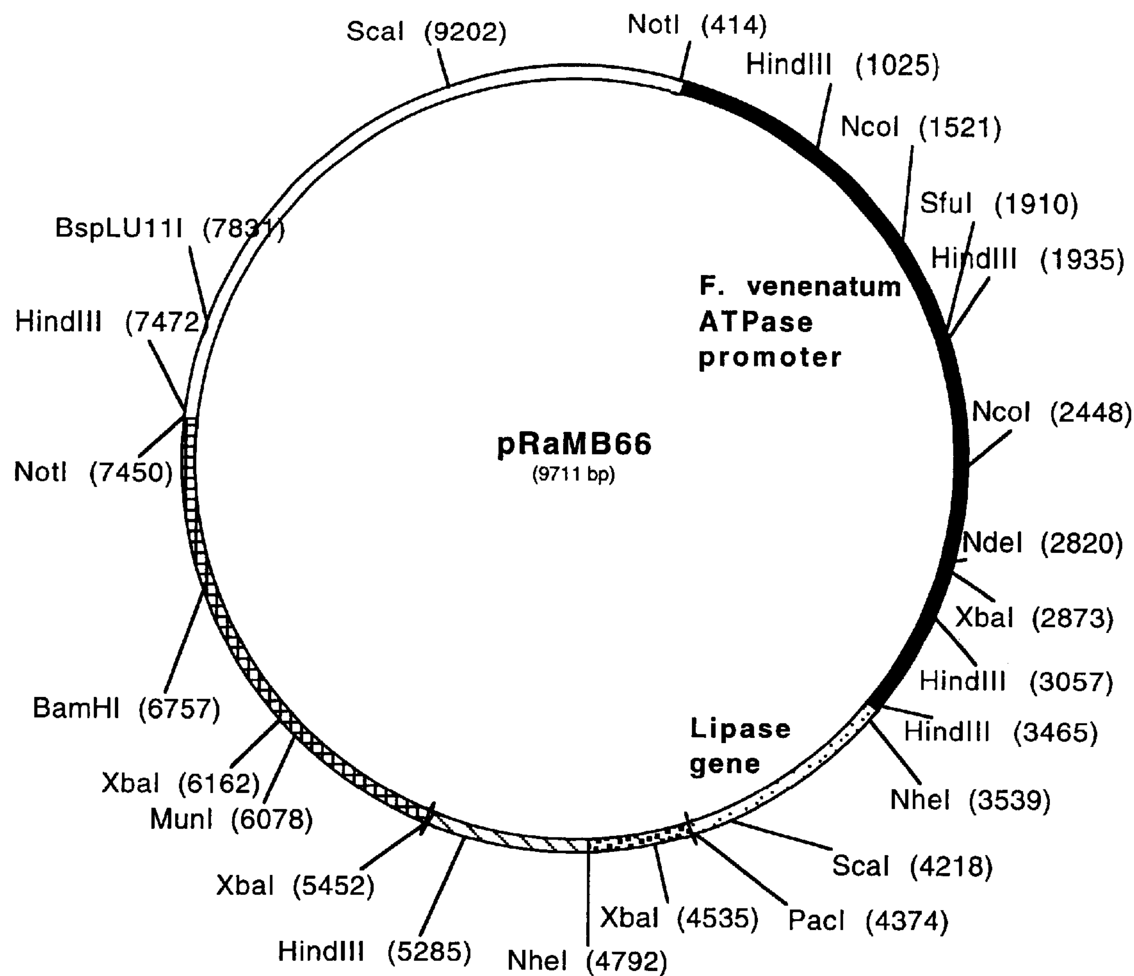
FIG. 13 shows a restriction map of pRaMB66.

The 3.1 kb amplified DNA fragment was subcloned into pCR-Script (Stratagene, La Jolla, Calif.) to generate the intermediate plasmid pQUINN-promoterA. Two restriction fragments were isolated from this plasmid; a 2.4 kb SmaI-NdeI fragment, and a 0.7 kb NdeI-NcoI fragment (together these segments span the entire promoter region). The isolated fragments were combined in a four-part ligation with the 8 kb PmeI-NcoI fragment of pRaMB60 and the 0.9 kb BspHI-PacI segment encoding the lipase reporter gene described in the previous examples. The product of this ligation, pRaMB66 (FIG. 13), contained the lipase reporter gene under the transcriptional control of the putative vacuolar associated protein gene promoter.

Example 20

Expression of the Lipase Reporter Gene in *Fusarium venenatum* Under Control of the AMG, "Daria" and Vacuolar Associated Protein Promoters Spores of *Fusarium venenatum* CC1-3 (MLY-3) were generated by inoculating a flask containing 500 ml of RA sporulation medium with 10 plugs from a 1×Vogels medium plate (2.5% Noble agar) supplemented with 2.5% glucose and 2.5 mM sodium nitrate and incubating at 28° C., 150 rpm for 2 to 3 days. Spores were harvested through Miracloth (Calbiochem, San Diego, Calif.) and centrifuged 20 minutes at 7000 rpm in a Sorvall RC-5B centrifuge (E. 1. DuPont De Nemours and Co., Wilmington, Del.). Pelleted spores were washed twice with sterile distilled water, resuspended in a small volume of water, and then counted using a hemocytometer.

Protoplasts were prepared by inoculating 100 ml of YEPG medium with $4\times10^7$ spores of *Fusarium venenatum* CC1-3 and incubating for 16 hours at 24° C. and 150 rpm. The culture was centrifuged for 7 minutes at 3500 rpm in a Sorvall RT 6000D (E. I. DuPont De Nemours and Co., Wilmington, Del.). Pellets were washed twice with 30 ml of 1 M $MgSO_4$ and resuspended in 15 ml of 5 mg/ml of NOVOZYME 234™ (batch PPM 4356, Novo Nordisk A/S, Bagsvaerd, Denmark) in 1 M $MgSO_4$. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC-:SPTC:DMSO to a final concentration of $1.25\times10^7$ protoplasts/ml. The protoplasts were stored at −80° C., after controlled-rate freezing in a Nalgene Cryo 1° C. Freezing Container (VWR Scientific, Inc., San Francisco, Calif.).

Frozen protoplasts of *Fusarium venenatum* CC 1-3 were thawed on ice. Five to ten $\mu$g of pRaMB62, pRaMB64, and pRaMB66 (described in Examples 17–19) and 5 $\mu$l of heparin (5 mg per ml of STC) were added to separate 50 ml sterile polypropylene tubes. One hundred $\mu$l of protoplasts was added to each tube, mixed gently, and incubated on ice for 30 minutes. One ml of SPTC was added and incubated 20 minutes at room temperature. After the addition of 25 ml of 40° C. COVE top agarose, the mixture in each tube was poured onto an empty 150 mm diameter plate and incubated overnight at room temperature. Approximately 24 hours later, an additional 25 ml of 40° C. COVE top agarose containing 10 mg of BASTA™ per ml was poured on top of the plate and incubated at room temperature for up to 14 days. The active ingredient in the herbicide BASTA™ is phosphinothricin. BASTA™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use.

The transformants were picked directly from the selection plates (COVE underlay with COVE-BASTA™ overlay) into 125 ml shake flasks containing 25 ml of M400Da medium supplemented with 1 mM $CaCl_2$ and 100 $\mu$g/ml ampicillin (to prevent bacterial contamination) and incubated at 28° C., 200 rpm on a platform shaker for 7 days. The untransformed recipient strain was also included as a negative control.

Flasks were sampled at 7 days. Cells were removed by centrifugation, and 10 $\mu$l of each supernatant sample was heated to 95° C. for 5 minutes with an equal volume of Tris-glycine sample buffer (Novex Experimental Technology, San Diego, Calif.). The denatured supernatant proteins were separated on a 10–20% Tris-glycine gradient gel (Novex Experimental Technology, San Diego, Calif.) and stained with Coomassie blue. SDS-PAGE analysis showed that the lipase-producing transformants secrete a prominent polypeptide with an apparent molecular weight of approximately 43 kDa.

Similarly, cell-free culture broths from each transformant were assayed for lipase activity using p-nitrophenylbutyrate as the substrate (Royer et al., 1995, supra).

The results shown in Table I demonstrated that active lipase was expressed and secreted using the *Fusarium venenatum* promoter elements present in pRaMB62, pRaMB64, and pRaMB66.

TABLE 1

| Vector used | Promoter | Transformant | Lipase yield (LU/ml) |
|---|---|---|---|
| None | — | negative control | <1.0 |
| pRaMB62 | glucoamylase | RaMB62.1 | 1158 |
| " | " | RaMB62.2 | 500 |
| " | " | RaMB62.3 | 1379 |
| " | " | RaMB62.4 | 1678 |
| " | " | RaMB62.5 | 702 |
| " | " | RaMB62.6 | 616 |
| " | " | RaMB62.7 | 473 |
| " | " | RaMB62.8 | 894 |
| " | " | RaMB62.9 | 564 |
| " | " | RaMB62.10 | 1036 |
| " | " | RaMB62.11 | 2731 |
| " | " | RaMB62.12 | 1960 |
| " | " | RaMB62.13 | 1682 |
| " | " | RaMB62.14 | 572 |
| " | " | RaMB62.15 | 1421 |
| pRaMB64 | "Daria" | RaMB64.1 | 1217 |
| " | " | RaMB64.2 | 561 |
| " | " | RaMB64.3 | 875 |
| " | " | RaMB64.4 | 839 |
| " | " | RaMB64.5 | 1449 |
| " | " | RaMB64.6 | 354 |
| " | " | RaMB64.7 | 377 |
| " | " | RaMB64.8 | 184 |
| " | " | RaMB64.9 | 1967 |
| " | " | RaMB64.10 | 657 |
| " | " | RaMB64.11 | 883 |
| " | " | RaMB64.12 | 184 |
| " | " | RaMB64.13 | 1935 |
| " | " | RaMB64.14 | 1049 |
| " | " | RaMB64.15 | 875 |
| pRaMB66 | Vacuolar associated protein | RaMB66.1 | 1990 |
| " | " | RaMB66.2 | 165 |
| " | " | RaMB66.3 | 380 |
| " | " | RaMB66.4 | 155 |
| " | " | RaMB66.5 | 170 |
| " | " | RaMB66.6 | 145 |
| " | " | RaMB66.7 | 180 |
| " | " | RaMB66.8 | 420 |
| " | " | RaMB66.9 | 200 |
| " | " | RaMB66.10 | 195 |
| " | " | RaMB66.11 | 190 |
| " | " | RaMB66.12 | 165 |
| " | " | RaMB66.13 | 140 |
| " | " | RaMB66.14 | 435 |
| " | " | RaMB66.15 | 125 |

Example 21

Comparative Expression of the *Humicola lanuginosa* Lipase Reporter Gene Under Control of *Fusarium venenatum* Amyloglucosidase and *Fusarium oxysporum* Trypsin Promoters

*Fusarium venenatum* CC1-3 transformants containing either pRamB64 (Example 17) or pDM218 (Example 13), prepared as described in Example 20, were cultivated for 180 hours at 29° C., 1200 rpm, pH 6.25 in 2 liter fermentors containing suitable carbon, nitrogen, and trace metals sources and supplemented with either urea or ammonium phosphate as the feed. Cell-free culture broths from each fermentation were assayed at 18 to 24 hour intervals for lipase activity using p-nitrophenylbutyrate as the substrate (Royer et al., 1995, supra) for 180 hours.

Figure 14:
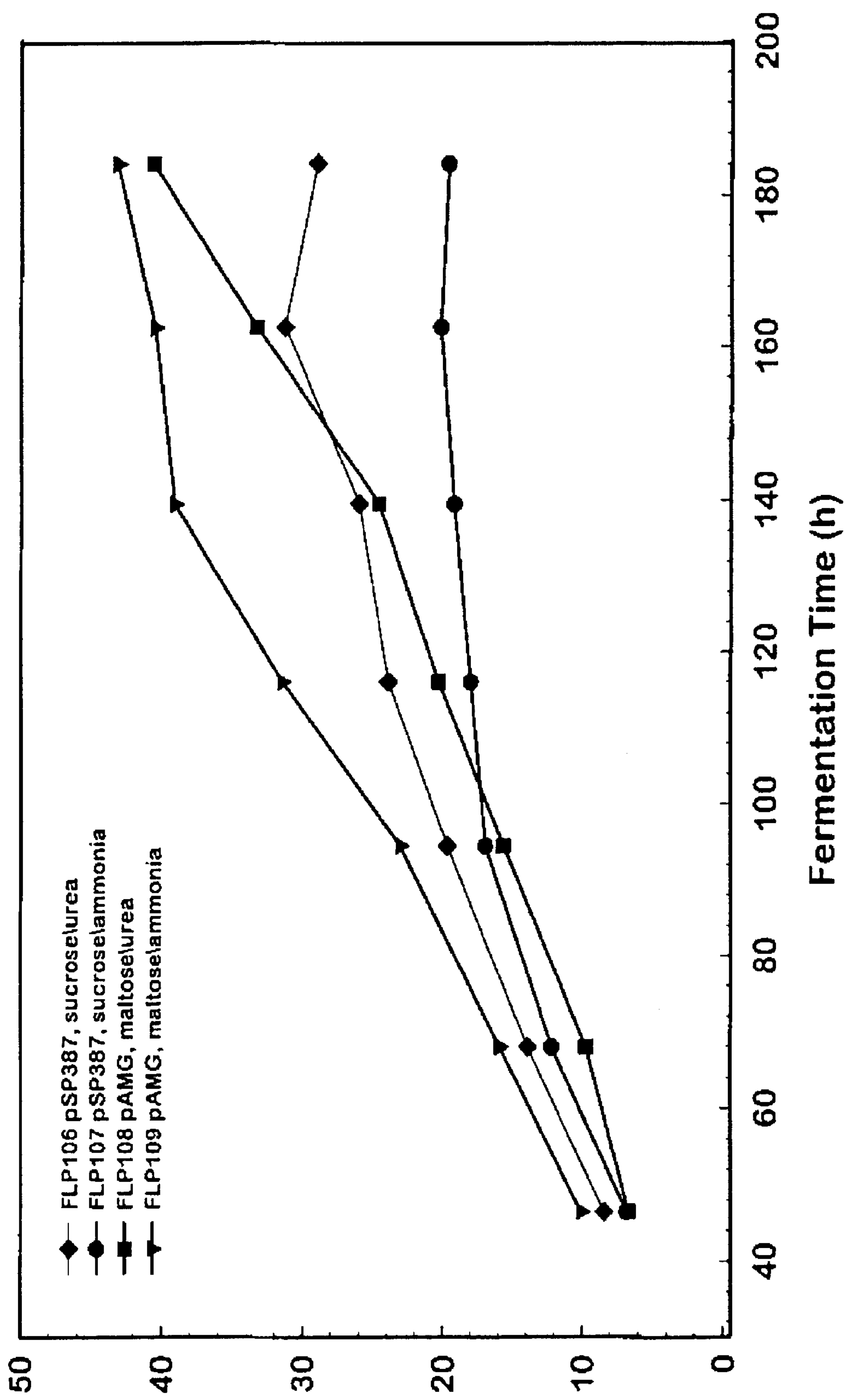
FIG. 14 shows comparative expression of a *Humicola lanuginosa* lipase reporter gene in *Fusarium venenatum* under control of *Fusarium venenatum* amyloglucosidase (pAMG) and *Fusarium oxysporum* trypsin (pSP387) promoters.

FIG. 14 shows comparative expression of the *Humicola lanuginosa* lipase reporter gene in *Fusarium venenatum* under control of either the *Fusarium venenatum* amyloglucosidase (pAMG) promoter or *Fusarium oxysporum* trypsin (pSP387) promoter. The results demonstrated higher levels of lipase activity with the *Fusarium venenatum* amyloglucosidase promoter than the *Fusarium oxysporum* trypsin promoter whether urea or ammonium phosphate was used as the source of nitrogen in the feed. Moreover, higher levels of lipase activity were observed using ammonium phosphate in the feed Deposit of Biological Materials The following biological materials have been deposited under the terms of the Budapest Treaty with the Agricultural Research Service Patent Culture Collection, Northern Regional Research Center, 1815 University Street, Peoria, Ill., 61604, and given the following accession numbers:

| Deposit | Accession Number | Date of Deposit |
|---|---|---|
| *E. coli* TOP10 (pECO3) | NRRL B-30067 | Oct. 27, 1998 |
| *E. coli* TOP10 (pFAMG) | NRRL B-30071 | Oct. 27, 1998 |
| *E. coli* DH10B (pQUINN) | NRRL B-30076 | Oct. 27, 1998 |
| *E. coli* TOP10 (pFB0346) | NRRL B-30073 | Oct. 27, 1998 |

The strains have been deposited under conditions that assure that access to the culture swill be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for producing a polypeptide, comprising:

(a) cultivating a fungal host cell in a medium for the production of the polypeptide, wherein the fungal host cell comprises a first nucleic acid sequence encoding the polypeptide operably linked to a second nucleic acid sequence comprising a promoter foreign to the first nucleic acid sequence, wherein the promoter comprises a nucleic acid sequence selected from the group consisting of (i) nucleotides 1 to 938 of SEQ ID NO:2; (ii) a subsequence of (i) that retains the promoter activity of nucleotides 1 to 938 of SEQ ID NO:2; and (iii) a nucleic acid sequence that hybridizes under medium stringency conditions with nucleotides 1 to 938 of SEQ ID NO:2; and (b) isolating the polypeptide from the cultivation medium.

2. The method of claim 1, wherein the promoter comprises nucleotides 1 to 938 of SEQ ID NO:2, or a subsequence thereof that retains the promoter activity of nucleotides 1 to 938 of SEQ ID NO:2.

3. The method of claim 1, wherein the promoter comprises the nucleic acid sequence contained in pFAMG which is contained in *E. coli* NRRL B-30071.

4. The method of claim 1, wherein the promoter comprises a nucleic acid sequence that hybridizes under medium stringency conditions with nucleotides 1 to 938 of SEQ ID NO:2.

5. The method of claim 4, wherein the promoter comprises a nucleic acid sequence that hybridizes under medium-high stringency conditions with nucleotides 1 to 938 of SEQ ID NO:2.

6. The method of claim 5, wherein the promoter comprises a nucleic acid sequence that hybridizes under high stringency conditions with nucleotides 1 to 938 of SEQ ID NO:2.

7. The method of claim 1, wherein the promoter is a hybrid promoter of fragments of two or more promoters, in which one or more fragments are fragments of nucleotides 1 to 938 of SEQ ID NO:2, wherein each fragment contributes to the activity of the hybrid promoter.

8. The method of claim 7, wherein the hybrid promoter further comprises one or more fragments of a different promoter.

9. The method of claim 1, wherein the promoter is a tandem promoter comprising one or more copies of one or more nucleic acid sequences selected from the group consisting of (a) nucleotides 1 to 938 of SEQ ID NO:2; (b) a subsequence of (a) that retains the promoter activity of nucleotides 1 to 938 of SEQ ID NO:2; and (c) a nucleic acid sequence that hybridizes under medium stringency conditions with nucleotides 1 to 938 of SEQ ID NO:2.

10. The method of claim 9, wherein the tandem promoter further comprises one or more different promoters.

11. The method of claim 1, wherein the first nucleic acid sequence encodes a polypeptide heterologous to the fungal host cell.

12. The method of claim 1, wherein the polypeptide is a hormone, enzyme, receptor, antibody or portion thereof, or reporter polypeptide.

13. The method of claim 12, wherein the enzyme is an oxidoreductase, transferase, hydrolase, lyase, isomerase, or ligase.

14. The method of claim 1, wherein the fungal host cell is a filamentous fungal cell or yeast cell.

15. The method of claim 14, wherein the filamentous fungal cell is an Acremonium, Aspergillus, Fusarium, Humicola, Mucor, Myceliophthora, Neurospora, Penicillium, Thielavia, Tolypocladium, or Trichoderma cell.

16. The method of claim 14, wherein the yeast cell is a Candida, Hansenula, Kluyveromyces, Pichia, Saccharomyces, Schizosaccharomyces, or Yarrowia cell.

17. The method of claim 14, wherein the filamentous fungal host cell is an Aspergillus cell or Fusarium cell.

18. An isolated promoter sequence comprising a nucleic acid sequence selected from the group consisting of (i) nucleotides 1 to 938 of SEQ ID NO:2; (ii) a subsequence of (i) that retains the promoter activity of nucleotides 1 to 938 of SEQ ID NO:2; and (iii) a nucleic acid sequence that hybridizes under medium stringency conditions with nucleotides 1 to 938 of SEQ ID NO:2.

19. The promoter sequence of claim 18, comprising nucleotides 1 to 938 of SEQ ID NO:2 or a subsequence thereof retaining the promoter activity of nucleotides 1 to 938 of SEQ ID NO:2.

20. The isolated promoter sequence of claim 18, comprising the nucleic acid sequence contained in plasmid pFAMG which is contained in *E. coli* NRRL B-30071.

* * * * *

SEQUENCE LISTING

```
<160> NUMBER OF SEQ ID NOS: 40

<210> SEQ ID NO 1
<211> LENGTH: 6050
<212> TYPE: DNA
<213> ORGANISM: Fusarium

<400> SEQUENCE: 1

aatttcgtcg atagcgaggg actcctggcc ctcgaattta gttagcgtat cagtgtaaag     60

tgctgggttc tccaggcgta agtaaattga accagatgtt agctcccaga tttcgccccg    120

aagccggttg ggcagaccaa cgcggataag tttatggaaa gttggttggc ggatcaatgt    180

aaagttcctg ccattgtcac gcagatactc ggcccaaaga cgcatctttg ccctatcgcg    240

caactttttt gggtccccag gatatcggaa gagcattcct aagccagcat ctggtgggag    300

atcgttcttc ttatcttcgg ttcttaaaag atgttcagag taacactcag cagcaactcg    360

acgcaacttg gctacgttgc caacgcctgc tctaagaccc ttcttgaggc cgtcacagaa    420

acgttcgcag gactgtctgg ttccagcgag atggattgtt atgcgttgtt ctcgggggtc    480

tctcttgtct ttagaggtat cggcaagaag gccattccac gtagtcagag cgagtgcgaa    540

ctataaccag gcaacgtcag aatttgtacc atgcaagatt tttataccac atacctggaa    600

gttctggcta ttcaagcgct ctacccttcg tatagcacat aaaggaaatg tgaatccatt    660
```

-continued

```
gccactgggt cctcctccgt gtgtctggcc ggtaaaagcg gtcgaggttg aaaggctagc    720
agattgcaca aagctagtgg gtgttgttga gaagcacatg taatgctctg acaggtgtag    780
cttgccagca taatgccatc ctcgatcgtg atccttatca ccgtgagtag cgttggaggg    840
cgggatagta agctcggcgt tgatctcgta gaggggcgcc tgagaggcgg gcaagcgaaa    900
ttggctctga aatagcgatg actttgaggg attccgatct gaactggata gattgagccc    960
ctgggtagga tcgataagct gctgggcttt ttgaacgatg ttggtgaagt tcgaaaacat   1020
gatttcggtc agcggcgcat gacgaggggg gttccggtcc aggagggagg tcgcggctga   1080
gcttgaagga gatgcaagac acgaagcgaa agacacgaag agagcgcaag agtctgagta   1140
tgtgcaacca ggctcgaata agtgcaaggc aggcagaagt acggaataga cgatagaatt   1200
gagtatagaa aggctgaatg gaagatggag acgagttata ggacggtgga gatagagtgg   1260
agttgaagtt gaacgaagct gcgtcaggtc cagatacggg agactggcca tcaactactg   1320
gccaggtagc cagggcgcga tgggcgggtg ggcagggtcg cggggggggac ctcagggcat   1380
tcctttctcc aagggccgct ggggctatgg acggggctgg ctgaactcca gccgtcatgg   1440
gatagcggtg caagagatca ggtactaagt ctaccatgat aatttagggg gcagagaaaa   1500
atgatatatt tgtttagtag taagcgggtt tttacagttg aggaaccaac cttcttcatt   1560
tatttattct ttctttctct gcaattcagt cctttttctt aaatagaata tctaccaatg   1620
gaacggcgtg gctgaagtgg ctgaagaata tagctcgagc tgtcaaaccg ctcatcctac   1680
taccctaggt ataaagctgg gaactaagac tcatttctat ccaactcatc atattgggag   1740
ttagtgtaga cctgtcggcc tagagaatat gtgtatctgc atactttcaa ataccctacg   1800
tatacccact atgtttagca caatcattga cctctcaagg cctcacccat ctcaacacct   1860
gtcgtgtgct cacttgacta cttctttgaa ccagctcgcc atcggactag tcgaacaagc   1920
ttgtcgcccc catacagatg aatgtatgtt taaagctaca tgatcagcct gaaccgagca   1980
taactcgagt gccgagactc ctctgatgta tatcgagatg aatgacaaac ctacgggtcc   2040
gttcttgaga agtggcctga gatttctcac ttggtgagaa aaaggacggg cgagcgggag   2100
cctgagtcag aagaaatacc tgtctccttg gatctcacat gacggtgttg tggaagagtg   2160
catctattgt cattgctgga gtgacggcag agtaggggtc taaagaaacc catactgagt   2220
agagatggag aagacaacaa aagcccaaga cgacagagac gacagaagat taaagctatc   2280
agagcgagac tatatcacta ttcgaaacct gcgagtaatt taacaagaag tacacatcat   2340
cattgttatc aattcgacga agacatggtc gaaaattctt gcggtgtata tgtctgttgt   2400
atatgggcct gggcattgtt atttttcgcc gtctttatgt gtactaacac ttccattgat   2460
accccagaac aaaagatgaa cgcttaaaca gcaccaaaat caggagaaga atggcgctgc   2520
tctaggtatg cttctgggat aaaaagcgat gttgatacct ctcagaaaag aagtgatttg   2580
aagttgaatc aaacaaatag ccgatggagc gatctgaagg ggtggcagac ctgctacgcg   2640
catttaggca aggcatcaac tcggcagatg attaagaaag gttttgtagg ttcacgtgtt   2700
gtgttgtgtt ccattataag tttataacct tgctaagatg caacgactct gacctcaggg   2760
tgttagaaaa attgaccact aggagcataa gtgacgaaat tcggggatca agacaataga   2820
tagtttcatt ttcatgtgct cctacgtctt ttcacgtaat gtttcttata aaaaaaaaga   2880
tagcattgtc tctttggtga aaagagaaaa aaagatgtta cgacgtggcc ttgattcgaa   2940
cagacgcctc cgaagagaat agatttctag tctatcgcgt tagaccactc cgccaccacg   3000
ccttacgtaa tctgtgattg ttgaaagtta ctctcgtgtt acggtctata cgtgaagaat   3060
```

-continued

```
ctacacttga cgagtctcga ggtctggggt cagttagacg gaaatgggag aacaaagaga   3120
cttggtgaca ttgcaggcaa ccgggtagat gttgaggtca ttgatcggac aagattgttg   3180
cttcaaaagt aacaggtatt ctttttttta atcaacagaa acgttccatg ttcatttgtt   3240
aatccaatct atttgtgata gcgtttgatg acaaacaata ataatgatgg tctggcggct   3300
agtgatcgtt tgtaatgacg tcgtcatata tcctatcact atacagttgc tttgcacacg   3360
cactcacgtc cttcattcgt tgtcttcact atttgatggt gatttggttc aacaacctac   3420
agaaataatg acctgtggtg ttctccgaat atggctagac caacacaagc ttgtaccgcg   3480
gcattcaaat caccatgtga tgcccatcat cagatcatcc accaacccaa aaacagacca   3540
actactcaca aaaaggcatc tcatcaagaa aaaacggcca actaacgtcc aaaaggcccg   3600
aaaaacgtcc atcacgccgc agccgagact tcaatagact gcacaagaag gaccgatgag   3660
atcgaccaga ctaaacccgg gagagtgtca aatatgcggg ggattgggga acttacccca   3720
gaaaagagaa ggaggataaa ttccatgtct ggggttgacg tctctattgg ttagacacga   3780
acgcctgctc tcggcgtaat ttataccata gcgccaatga gggcggaaac tcctgttttg   3840
tcaagtcgtc attgttggtt gggtcatgat atatagccag taggtatccg tcttggtgat   3900
tgaccagaca tatcgctcat cacagatcaa catcactgct atcaccaaca tgcttactca   3960
agtcctttat ggcttggtag ccagtgccct ttggcaaggc caagtcgttg catcaccaag   4020
caaggacaat tcactggagc gcttcattga caaacaagct gatatttcta tcaagggtgt   4080
ccttgctaat attggcgctg atggaaaaag ggcacagggt gcagcgcctg gtgctgttgt   4140
ggcaagtcca tcgaaagaag atcctgattg taagccagca tcctaccttg tccttgtccg   4200
catgctaatg atggtctcag attggtacac ttggactcgt gactctgctt taacgtacaa   4260
agtgctcgtt gagagattca tccacggcga caaatctctc caacgaaaga tagatgaata   4320
tgtctccgca caagcgaaac tgcaagggac cacaaatcca tcgggcagcc cagagtcggg   4380
cggtctcggc gagccaaagt tccatgtgaa tctcactgct ttcactggat cttggggtcg   4440
gcctcagcgc gacggccctc cgcttcgggc taccgccttg actctgtatg cagaatggct   4500
catttcccac ggcgaaagat ccaaggcttt gaacaaagtc tggccagtca tcgagaagga   4560
ccttgcgtat actaccaagt tctggaatcg cactggctat gatctatggg aggaggttaa   4620
tggatcttct ttctttacac tttcggcttc gcatcgtgct cttgtcgaag gtgccgctct   4680
ggctaagaaa cttggcaaat cttgtcctga ctgtgtcacc aacgctcctc gcgttctgtg   4740
cttccttcag actttctgga ctggtggcta cgttgactcc aacattaacg tcaaggatgg   4800
tcgcaagggt ctcgatgtca actccatcct ctcgtccatt catacattcg atcccaactc   4860
caagtgcacc gactcgacgt tccagccttg ttcacccaga gctcttgcga accacaaggc   4920
ggtcgtcgat tctttcaggt caatctatgg tgtcaacaag aatagaggtc aaggcaaggc   4980
cgcggctgtt ggtcgatata gcgaggacgt gtactatgat ggcaaccctt ggtacctggc   5040
cactcttgct gctgcagaac aactctacgc tgcggtctac cagtgggata agcttggcgc   5100
tgttactgtt gacgatgtat ctttgtcttt cttcaaggat atcgttccca aggtctccaa   5160
aggcacttat gccaagaaga ccaagacata caaggagatc atcaaagcag ccaagactta   5220
cgccgacggc tttgtcgctg tcgtgcagac atacactccc aaggacggct cactagctga   5280
gcaatttgac aagtcaactg gagcccccaa gtccgctgtt cacctcacct ggtcctacgc   5340
cgcctttgtc gccacaactg aacgtcgcga cggcatcatc tctccctcct ggggcgaaag   5400
```

-continued

```
cagcgccaac aaggtccccg ccgtgtgtca agctgcccca gcatgtgaca caaccatcac   5460

cttcagtgtc aagaacgtgc aagtttcatc cgaccaaaag gtttacgtgg ttggctcagt   5520

gactgagctt tctaactggt cacctgatga tggcattgcg cttacgccat ctagttccgg   5580

agtgtggagc gtcaaggtta agattccttc tgatacaagc tttgagtaca agtatatcaa   5640

gaagactagc agtggggatg ttacgtggtt gagtgatccc aacaaccggg ctattacggg   5700

tagcaagtgt ggaagtacaa gtactcttga tgatgagtgg aggtagtgga tgacagattt   5760

atcaagctat gtagttttgt gaatatataa ttatccaaat tatcagggtt cggtaagaat   5820

ataattcagt tcagcagtct gtacaagcaa gccatgattc acgcttcctt cgtttggaag   5880

ataagggttc ctcgccaccg tcaagataat tttctcgtgc taatatcacg taatccatct   5940

gcattaaacc cttgccggga aggtttcttc aacccagcaa ccccagagta actcggagat   6000

agggaagtct atttgcctta tcctccgtga cgaattccct gaacccaatt              6050
```

<210> SEQ ID NO 2
<211> LENGTH: 2517
<212> TYPE: DNA
<213> ORGANISM: Fusarium

<400> SEQUENCE: 2

```
aattactact gtgatgtgat cacacctaac taaataccta actcacccga tggatcgaca     60

aggaaatctc acgcccttgt cgagtctcct ctttcgtctg tctcctgggc tcgctactgt    120

ccgattgtaa ctctcgctct ccaacttgtt caactctaat aagtggtggc acaacgtgaa    180

gatgtattgt tgtgtgaggc ggggggttgc gtggcattac caaagagacc aaaagtcccc    240

ctatgtcgat ttgatggtgt tgcgttgcca tgatacggga ccccgaatat gttgtatgca    300

tcatgcgtac agaaagctac tgttcaaaac gaacggcaaa gcggattgat caacccgtga    360

aagaccatgg gtctctctca gtccacaatc ttctcttcct gatcaaattt atggatccaa    420

gcggccacaa ttctagcgcc atcatgggtc cctttcctct tttcgctcac cccatgttcc    480

ctgtcccacc tcattcagtg gacctgatgg atccctatcc cccgatgagc cggggggtgc    540

agccttggcg ctctcttctt gttagtgtga cctactgttg atttcactca gcagtcctag    600

agtccattta gttgggcctg gggtgatggg gtctgagact ttgcttcttg cctggtcttg    660

tctagctcga atctgtgggt tgcctggcct ggcctggcct gacctgacct gaggggggtg    720

ccccttttgct ctgttctgca tatgttgcta ttagctacct actcgagaat tcataaaagg    780

actgtccagc cccgtctctt actgacttct ttcctttccc tcttcaccct cgttgtcata    840

tcaaatctgt cactcgttag accagactac cattcccact ttcgctttta aactacttta    900

ctcaactaat tctaatacca actccaaaaa ccatcaacat gcgtttcaca tcaatcctcg    960

ctgccggcgc tttcgccacc atggccgctg cccagagcaa gaccgtctcc ctcgaccctg   1020

ctcagcagtc tcaggccgac tgcctctccg actgtgagcc tggcgatgtc aagtgccagt   1080

cttactgcat cactgtatgt tacaacaacg attcccctgt catgtgtaga aaactaacaa   1140

tcccaatagg ttccctctcc tgacgagaag aacatcgagg aaaccaccaa gtgttgtttg   1200

ccgcctgccc caagggcaag ggctccgaag gccgacactg agaagtacac cgtttgcatg   1260

aacgagtgta tcgccgacaa ctactggaag tccgttgatg gtaccccccg tggcaccgac   1320

gtccccgatg tcaagagcaa ggcctccgag gctgcctcct ccgctgctga gaaggccacc   1380

gccaccggta ctgctgctga gtctgatgct accgccactg gtgcctccgc tactgagtcc   1440

gagtccggct ccgactccag ctccgaggag accggctctg cctctggcac tgccactggt   1500
```

```
accgctgctg aggtctccga gactggtaac gccgcctctt ccctcgttgg tggtgtctcc   1560

ttcctcggtc tcgttgccgc tatcttcgct ctgtaaattg ggtttcctgc tttaggataa   1620

tctgatttgg catgacggag aaggatttaa tgggttttat tacagcggta atgattggag   1680

tttggatttc aagatgtgac acgttggaca gcatgataag gcctacgggt ctgatcaatt   1740

tcatggacaa attttgtttt tttgggtaat catttcgcgt tcacatatgg ctcggcatat   1800

gagcatgaat acaatacctc ttttttgcgc ctcaattcat tccaatttct tgtgatctca   1860

cagtgattca acttacaagt tgcggcgcga ccactgaggt cgtgtctgat gtgggtcttc   1920

tgtttgtgat tggctcatga ttcccaatcg ggtgcttcaa acgttagttt gtaaacaagc   1980

gaaatgaggg tcttaggatg catgttcaaa gcgcaaaacc caattgaatt caaatgttaa   2040

agaatcatcg agaagagcga gttactgagg tgaatttgtg ctttcaactg tcaatacctc   2100

cctcagaaca aatgaattga attattattc acactcaatg cccaatattc taaacatgtt   2160

cgttgtaaca gagttttaat tccttgacgc cacaatgttc cttggtaatt atcgcgcctg   2220

tcacatgaac tggctcctga acttaaacgt tggtgaccca gcaactcgtt tatcaggctt   2280

agggtagctg tcatacaaca aacaaacttg tacaattgat gttattgatg aatcatgtat   2340

agaagagcac aattgattta aacacagata aactggtcga accgatttta tcaggttgtg   2400

tgaacatgca ttgccgaatc agaaaccaga gtaagactat ctacagttcc atgaagacaa   2460

ttcacagact gccagaaagc aaggtactgg aagcacgaga gacaaaatta ttgaatt      2517
```

<210> SEQ ID NO 3
<211> LENGTH: 4047
<212> TYPE: DNA
<213> ORGANISM: Fusarium

<400> SEQUENCE: 3

```
aattagagag gttagggatt tcacatggcc accaatggga aggaggcaac catctgcacg     60

agcccaccaa gtcatctcct caaactgtgc tgcgactaag aatttgattc cggttctggc    120

ctggcctttg tatcagctag gtcattctcg actaccggag gccaggctga agcagtcagt    180

cacgcattgt cactttatcg gtcctgtcct catacggata cactaggcgt caatgggctt    240

caaacggaga tccagagatc tcatgaagag catcgacgat aaagtgagtg gttggggata    300

ctgtgcggtg ccgaccccag cggcagccag gttccaccct tgattacatg gttgaaaagt    360

ggcgttactg ggcgagatca aatttggcat gtatgttcgt ccaatgacgc gagctctcca    420

tgttgctgcg agggtcagga acggaccagc atgggatcag tgaggtgaaa tccaaccgag    480

ggagagcgag atctttgtgc tcatatccat gctgccatgc tacgtgccga acaggccaga    540

tggcgttcaa ctcagtcgac caggtccgat gaacgcggag cggtgacgag atcgaagctt    600

catctatcgc ttacggggtt atgttccact ttccattaac gtttgcgagt tgctgtttga    660

gagccatgtc gaaagcatgg accgtgtcac atctttcaag gtaaatctgg aggtgggaag    720

aagaattgcg aggaacagga tgggaggata gcaggctgac gcggaaagct aggtagctac    780

ctggctgatt actggctaaa gctggagagc aactaggtaa tatcaggcaa agagctccaa    840

gagctattgg gaggctggct gattgtctct ggctgagacg caggaggaag ggttaaaatg    900

gccggcaggc caagaagggg ctgcaaaaca cggagtggat ggtggggcct cccacatacg    960

ggattcgggc tgcggatcta acctcaattt ggcaagaggt aaataggacg acatgcaggc   1020

cccctgacat gtaaacaaga caagtggtaa acaagccatc aacatcaaca agagcgaaca   1080
```

-continued

```
atcgacacac ccatgggggt gagatatggt agtaaggcag agagagatca gggcagcata   1140
cgtgggaaag ggctgggcaa gaaaggacac aacggatcaa cagaacgcag cgctaccgag   1200
ggagcaacac aagtacagta accgctcaca gaggcacaac tcgtccaatc ctgccccccgt  1260
cttcaaaagc ccagtttcgt tctgagtcct gtccggtccc tcttctcctc ctactccctc   1320
caattatcgc catccacatc gacatcgtca attcacaacc tcacccagac aagaagaaaa   1380
gaacgactga aggccttcgc tcgccatcac ccgattcttt tccattctct tcgacttttg   1440
tttcgtagga acaagagcca gagaacttct tgtcatcctt tcgaatttcg gaaggttgta   1500
tgagaagctt ctctcgcgcc agcaaaagtc gcaaatctgg actttgaggc acgcgtcccc   1560
gttcccttca gcatcttccc atcgacatat cgggaatccg aatcccacac acagaccgtt   1620
accgaaacaa agatacacga agaggttgag atcaaacccc aacagcccga agccggacgg   1680
gaaggtgaaa tatcttctgt ctccgtcacc gccgaacagg tccctcctcc tcgtcaagag   1740
caagagttta tcgaagaaga ggtccatatt acgcgtgaag aagaacatta ccaccgtccc   1800
ggtgtccaaa aattcgagca cgaagacttt actatccgtg aagactcccg acggtacgtt   1860
cgattttaca tttcctttca tctccattta ggtcgcatct tttcgttac ttttttggtc    1920
aattacacgg gggatacgat tttcccacgg tcggagaaag ccctgcttgc tctctatgcc   1980
taggtctgta ttctctcatc cctctgcgct gatctggcca tggagacgtg tgagaacaag   2040
actacaattc atcacatcat ttttcgctag gcgaaagcaa ttaccgttgt ccccgacctt   2100
ctcccaacca tcagttttca ctttcccttt tcttggtctg gcttgccttg accattaccc   2160
accgcgcacg gagcgcttca gtccccagcc atcccattct cacatcactt ctcatatcct   2220
ctcttcacac gcctcacaca cccacccccct gcatgctacc atgccaaccc acttcagctt  2280
ggctggatac ccaatttgct ttgcttcctc cccggctcac tagcgcctct aagcctgctg   2340
gcctgagcaa ggcggtggag ctatctcagg ggccgccgcc tcccgttgcc atatgatacg   2400
caaacgactt actatagaca tccatcagct aacccagaca aatctagacc tcaacctccc   2460
tctcaatacc aaccttccca gtaccaccaa ccttcccact accaaccacc tcccaaattc   2520
caaacttctc acactcacgt agagatcgac acccaccgtc atccctacta ctccaccccc   2580
attgatctcg ctgaacgtga ataccgccag cgttaccgcc ctgcccaagc tttttccaca   2640
gaagaccctt cttcccactc tcatcctcac taccaacctc aagacaactt caaagccaac   2700
aactacaccg ttgaaggccg acccgctccc caattccatt cctctgagaa gactgaaatc   2760
aacaagttta ctgttgacga acactcctct cgccctcagt acaaccacac cgagaagacc   2820
gaattcaaca actacactgt tgacagccga tcttcccgtc ctcaatacaa cacctgtgag   2880
aagactgaga tcaacaattt cactgttgac gcccgctctt cccagccacg gtaccgcgac   2940
accaagacaa ctcaagtcaa cagctacgcc gttgacaagc ccgtttctcg tccatcttac   3000
aagaaggacg tgagatttac tgaacaaacc gtcgaagctt caaagtccga caagtccaag   3060
atgggttact acgacgacga gggtaagtga aatctgtcac ccagcgagcg ccatcaagct   3120
ctctattcgt gacgcaattc aagctaaccc agtcaccagg ttctttccgc aacggcggca   3180
tccacaagct cggtgacaag tcccgcgaca ttgaggttga cattcgcgag acttctcgtc   3240
ctgccaatga ctgcgctccc aacaccgtca gcatcccctg ccaccacatc cgtctgggtg   3300
atttcctcat gctccagggc cgcccctgcc aggtcatccg catctccacc tcctctgcca   3360
ctggccagta ccgctacctt ggtgtcgacc tcttcaccaa gcagcttcat gaggagtctt   3420
ctttcatctc caaccctgcc cccagcgttg tcgttcagtc catgctcggc cctgtcttca   3480
```

```
agcagtaccg tgtcctcgat atgcaggagg gtcagatcgt tgccatgacc gagactggcg   3540

acgtcaagca gggtctccct gtcattgacc agtccaacct ctactctcgc ctccacaacg   3600

ctttcgagtc cggtcgtggc tctgttcgcg tcctcgtcct caacgacggt ggccgtgagc   3660

ttgccgttga catgaaggtc atccacggct ctcgcctgta agcgtgttca actgttttct   3720

gaattcgggc agccgcttgc aatgcgactt cttcccaatg tttaattgag tgaagggaca   3780

gcactaccag tctcacctca actgtgggga gcgggtctgg gctgtctcta atcttacctg   3840

tacaatgtca agtttcatag ggacctgtt gtgtcaagat ggttcgagtt ttgtttgtgt   3900

caagattgga taaatgatat tggctagctg gaaatactgg agtcttttgt gtagatggga   3960

gagttctgta catgaactat agtaattgac aattgattcc gcatctactt agcttttcat   4020

tggtgctcta tgcccaacat gtgaatt                                       4047


<210> SEQ ID NO 4
<211> LENGTH: 581
<212> TYPE: PRT
<213> ORGANISM: Fusarium

<400> SEQUENCE: 4

Met Leu Thr Gln Val Leu Tyr Gly Leu Val Ala Ser Ala Leu Trp Gln
 1               5                  10                  15

Gly Gln Val Val Ala Ser Pro Ser Lys Asp Asn Ser Leu Glu Arg Phe
            20                  25                  30

Ile Asp Lys Gln Ala Asp Ile Ser Ile Lys Gly Val Leu Ala Asn Ile
        35                  40                  45

Gly Ala Asp Gly Lys Arg Ala Gln Gly Ala Ala Pro Gly Ala Val Val
    50                  55                  60

Ala Ser Pro Ser Lys Glu Asp Pro Asp Tyr Trp Tyr Thr Trp Thr Arg
65                  70                  75                  80

Asp Ser Ala Leu Thr Tyr Lys Val Leu Val Glu Arg Phe Ile His Gly
                85                  90                  95

Asp Lys Ser Leu Gln Arg Lys Ile Asp Glu Tyr Val Ser Ala Gln Ala
            100                 105                 110

Lys Leu Gln Gly Thr Thr Asn Pro Ser Gly Ser Pro Glu Ser Gly Gly
        115                 120                 125

Leu Gly Glu Pro Lys Phe His Val Asn Leu Thr Ala Phe Thr Gly Ser
    130                 135                 140

Trp Gly Arg Pro Gln Arg Asp Gly Pro Pro Leu Arg Ala Thr Ala Leu
145                 150                 155                 160

Thr Leu Tyr Ala Glu Trp Leu Ile Ser His Gly Glu Arg Ser Lys Ala
                165                 170                 175

Leu Asn Lys Val Trp Pro Val Ile Glu Lys Asp Leu Ala Tyr Thr Thr
            180                 185                 190

Lys Phe Trp Asn Arg Thr Gly Tyr Asp Leu Trp Glu Glu Val Asn Gly
        195                 200                 205

Ser Ser Phe Phe Thr Leu Ser Ala Ser His Arg Ala Leu Val Glu Gly
    210                 215                 220

Ala Ala Leu Ala Lys Lys Leu Gly Lys Ser Cys Pro Asp Cys Val Thr
225                 230                 235                 240

Asn Ala Pro Arg Val Leu Cys Phe Leu Gln Thr Phe Trp Thr Gly Gly
                245                 250                 255

Tyr Val Asp Ser Asn Ile Asn Val Lys Asp Gly Arg Lys Gly Leu Asp
            260                 265                 270
```

```
Val Asn Ser Ile Leu Ser Ser Ile His Thr Phe Asp Pro Asn Ser Lys
        275                 280                 285

Cys Thr Asp Ser Thr Phe Gln Pro Cys Ser Pro Arg Ala Leu Ala Asn
    290                 295                 300

His Lys Ala Val Val Asp Ser Phe Arg Ser Ile Tyr Gly Val Asn Lys
305                 310                 315                 320

Asn Arg Gly Gln Gly Lys Ala Ala Ala Val Gly Arg Tyr Ser Glu Asp
                325                 330                 335

Val Tyr Tyr Asp Gly Asn Pro Trp Tyr Leu Ala Thr Leu Ala Ala Ala
            340                 345                 350

Glu Gln Leu Tyr Ala Ala Val Tyr Gln Trp Asp Lys Leu Gly Ala Val
        355                 360                 365

Thr Val Asp Asp Val Ser Leu Ser Phe Phe Lys Asp Ile Val Pro Lys
    370                 375                 380

Val Ser Lys Gly Thr Tyr Ala Lys Lys Thr Lys Thr Tyr Lys Glu Ile
385                 390                 395                 400

Ile Lys Ala Ala Lys Thr Tyr Ala Asp Gly Phe Val Ala Val Val Gln
                405                 410                 415

Thr Tyr Thr Pro Lys Asp Gly Ser Leu Ala Glu Gln Phe Asp Lys Ser
            420                 425                 430

Thr Gly Ala Pro Lys Ser Ala Val His Leu Thr Trp Ser Tyr Ala Ala
        435                 440                 445

Phe Val Ala Thr Thr Glu Arg Arg Asp Gly Ile Ile Ser Pro Ser Trp
    450                 455                 460

Gly Glu Ser Ser Ala Asn Lys Val Pro Ala Val Cys Gln Ala Ala Pro
465                 470                 475                 480

Ala Cys Asp Thr Thr Ile Thr Phe Ser Val Lys Asn Val Gln Val Ser
                485                 490                 495

Ser Asp Gln Lys Val Tyr Val Val Gly Ser Val Thr Glu Leu Ser Asn
            500                 505                 510

Trp Ser Pro Asp Asp Gly Ile Ala Leu Thr Pro Ser Ser Ser Gly Val
        515                 520                 525

Trp Ser Val Lys Val Lys Ile Pro Ser Asp Thr Ser Phe Glu Tyr Lys
    530                 535                 540

Tyr Ile Lys Lys Thr Ser Ser Gly Asp Val Thr Trp Leu Ser Asp Pro
545                 550                 555                 560

Asn Asn Arg Ala Ile Thr Gly Ser Lys Cys Gly Ser Thr Ser Thr Leu
                565                 570                 575

Asp Asp Glu Trp Arg
            580


<210> SEQ ID NO 5
<211> LENGTH: 200
<212> TYPE: PRT
<213> ORGANISM: Fusarium

<400> SEQUENCE: 5

Met Arg Phe Thr Ser Ile Leu Ala Ala Gly Ala Phe Ala Thr Met Ala
 1               5                  10                  15

Ala Ala Gln Ser Lys Thr Val Ser Leu Asp Pro Ala Gln Gln Ser Gln
            20                  25                  30

Ala Asp Cys Leu Ser Asp Cys Glu Pro Gly Asp Val Lys Cys Gln Ser
        35                  40                  45

Tyr Cys Ile Thr Val Pro Ser Pro Asp Glu Lys Asn Ile Glu Glu Thr
```

```
    50                  55                  60

Thr Lys Cys Cys Leu Pro Pro Ala Pro Arg Ala Arg Ala Pro Lys Ala
65                  70                  75                  80

Asp Thr Glu Lys Tyr Thr Val Cys Met Asn Glu Cys Ile Ala Asp Asn
                85                  90                  95

Tyr Trp Lys Ser Val Asp Gly Thr Pro Arg Gly Thr Asp Val Pro Asp
            100                 105                 110

Val Lys Ser Lys Ala Ser Glu Ala Ala Ser Ser Ala Ala Glu Lys Ala
        115                 120                 125

Thr Ala Thr Gly Thr Ala Ala Glu Ser Asp Ala Thr Ala Thr Gly Ala
    130                 135                 140

Ser Ala Thr Glu Ser Glu Ser Gly Ser Asp Ser Ser Ser Glu Glu Thr
145                 150                 155                 160

Gly Ser Ala Ser Gly Thr Ala Thr Gly Thr Ala Ala Glu Val Ser Glu
                165                 170                 175

Thr Gly Asn Ala Ala Ser Ser Leu Val Gly Gly Val Ser Phe Leu Gly
            180                 185                 190

Leu Val Ala Ala Ile Phe Ala Leu
        195                 200
```

<210> SEQ ID NO 6
<211> LENGTH: 187
<212> TYPE: PRT
<213> ORGANISM: Fusarium

<400> SEQUENCE: 6

```
Met Gly Tyr Tyr Asp Asp Glu Gly Ser Phe Arg Asn Gly Gly Ile His
 1               5                  10                  15

Lys Leu Gly Asp Lys Ser Arg Asp Ile Glu Val Asp Ile Arg Glu Thr
            20                  25                  30

Ser Arg Pro Ala Asn Asp Cys Ala Pro Asn Thr Val Ser Ile Pro Cys
        35                  40                  45

His His Ile Arg Leu Gly Asp Phe Leu Met Leu Gln Gly Arg Pro Cys
    50                  55                  60

Gln Val Ile Arg Ile Ser Thr Ser Ser Ala Thr Gly Gln Tyr Arg Tyr
65                  70                  75                  80

Leu Gly Val Asp Leu Phe Thr Lys Gln Leu His Glu Glu Ser Ser Phe
                85                  90                  95

Ile Ser Asn Pro Ala Pro Ser Val Val Val Gln Ser Met Leu Gly Pro
            100                 105                 110

Val Phe Lys Gln Tyr Arg Val Leu Asp Met Gln Glu Gly Gln Ile Val
        115                 120                 125

Ala Met Thr Glu Thr Gly Asp Val Lys Gln Gly Leu Pro Val Ile Asp
    130                 135                 140

Gln Ser Asn Leu Tyr Ser Arg Leu His Asn Ala Phe Glu Ser Gly Arg
145                 150                 155                 160

Gly Ser Val Arg Val Leu Val Leu Asn Asp Gly Gly Arg Glu Leu Ala
                165                 170                 175

Val Asp Met Lys Val Ile His Gly Ser Arg Leu
            180                 185
```

<210> SEQ ID NO 7
<211> LENGTH: 30
<212> TYPE: DNA
<213> ORGANISM: Fusarium

-continued

<400> SEQUENCE: 7
gagctcgagg aattcttaca aaccttcaac 30

<210> SEQ ID NO 8
<211> LENGTH: 47
<212> TYPE: DNA
<213> ORGANISM: Fusarium

<400> SEQUENCE: 8
ttaattaagg tacctgaatt taaatggtga agagatagat atccaag 47

<210> SEQ ID NO 9
<211> LENGTH: 51
<212> TYPE: DNA
<213> ORGANISM: Fusarium

<400> SEQUENCE: 9
tcaccattta aattcaggta ccttaattaa attccttgtt ggaagcgtcg a 51

<210> SEQ ID NO 10
<211> LENGTH: 42
<212> TYPE: DNA
<213> ORGANISM: Fusarium

<400> SEQUENCE: 10
tggtatgcat aagcttgaat tcaggtaaac aagatataat tt 42

<210> SEQ ID NO 11
<211> LENGTH: 35
<212> TYPE: DNA
<213> ORGANISM: Fusarium

<400> SEQUENCE: 11
cagtgaattg gcctcgatgg ccgcggccgc gaatt 35

<210> SEQ ID NO 12
<211> LENGTH: 35
<212> TYPE: DNA
<213> ORGANISM: Fusarium

<400> SEQUENCE: 12
aattcgcggc cgcggccatc gaggccaatt cactg 35

<210> SEQ ID NO 13
<211> LENGTH: 34
<212> TYPE: DNA
<213> ORGANISM: Fusarium

<400> SEQUENCE: 13
cacgaaggaa agacgatggc tttcacggtg tctg 34

<210> SEQ ID NO 14
<211> LENGTH: 34
<212> TYPE: DNA
<213> ORGANISM: Fusarium

<400> SEQUENCE: 14
cagacaccgt gaaagccatc gtctttcctt cgtg 34

<210> SEQ ID NO 15
<211> LENGTH: 46
<212> TYPE: DNA
<213> ORGANISM: Fusarium

<400> SEQUENCE: 15
ctatctcttc accatggtac cttaattaaa taccttgttg gaagcg 46

<210> SEQ ID NO 16
<211> LENGTH: 46
<212> TYPE: DNA
<213> ORGANISM: Fusarium

<400> SEQUENCE: 16
cgcttccaac aaggtattta attaaggtac catggtgaag agatag 46

<210> SEQ ID NO 17
<211> LENGTH: 30
<212> TYPE: DNA
<213> ORGANISM: Fusarium

<400> SEQUENCE: 17
atttaaatga tgaggagctc ccttgtgctg 30

<210> SEQ ID NO 18
<211> LENGTH: 29
<212> TYPE: DNA
<213> ORGANISM: Fusarium

<400> SEQUENCE: 18
ttaattaact agagtcgacc cagccgcgc 29

<210> SEQ ID NO 19
<211> LENGTH: 45
<212> TYPE: DNA
<213> ORGANISM: Fusarium

<400> SEQUENCE: 19
ataagaatgc ggccgctagt ttaaacttac aaaccttcaa cagtg 45

<210> SEQ ID NO 20
<211> LENGTH: 19
<212> TYPE: DNA
<213> ORGANISM: Fusarium

<400> SEQUENCE: 20
tagcatctat ctccgtctt 19

<210> SEQ ID NO 21
<211> LENGTH: 19
<212> TYPE: DNA
<213> ORGANISM: Fusarium

<400> SEQUENCE: 21
gtgtgcagtg acccagaat 19

<210> SEQ ID NO 22
<211> LENGTH: 42
<212> TYPE: DNA
<213> ORGANISM: Fusarium

<400> SEQUENCE: 22
gattgggtcc ctacgtagtt aacactatag gccatcgttt ac 42

<210> SEQ ID NO 23
<211> LENGTH: 28
<212> TYPE: DNA

-continued

<213> ORGANISM: Fusarium

<400> SEQUENCE: 23
atttaaatat ggtttcttcg gcattcgc 28

<210> SEQ ID NO 24
<211> LENGTH: 28
<212> TYPE: DNA
<213> ORGANISM: Fusarium

<400> SEQUENCE: 24
ttaattaact attccgacgg aacaaagc 28

<210> SEQ ID NO 25
<211> LENGTH: 44
<212> TYPE: DNA
<213> ORGANISM: Fusarium

<400> SEQUENCE: 25
ctcttggata tctatctctt caccatggtt tcttcggcat tcgc 44

<210> SEQ ID NO 26
<211> LENGTH: 43
<212> TYPE: DNA
<213> ORGANISM: Fusarium

<400> SEQUENCE: 26
gcgaatgccg aagaaaccat ggtgaagagt agatatccaa gag 43

<210> SEQ ID NO 27
<211> LENGTH: 30
<212> TYPE: DNA
<213> ORGANISM: Fusarium

<400> SEQUENCE: 27
gaatgacttg gttgacgcgt caccagtcac 30

<210> SEQ ID NO 28
<211> LENGTH: 26
<212> TYPE: DNA
<213> ORGANISM: Fusarium

<400> SEQUENCE: 28
tctagcccag aatactggat caaatc 26

<210> SEQ ID NO 29
<211> LENGTH: 39
<212> TYPE: DNA
<213> ORGANISM: Fusarium

<400> SEQUENCE: 29
cttaactttg acttgaaaaa catatctgac atttgctcc 39

<210> SEQ ID NO 30
<211> LENGTH: 59
<212> TYPE: DNA
<213> ORGANISM: Fusarium

<400> SEQUENCE: 30
ggacggcctt ggctagccct ccgtgcggcc gccggccggt ctcgcaggat ctgtttaac 59

<210> SEQ ID NO 31
<211> LENGTH: 32

-continued

```
<212> TYPE: DNA
<213> ORGANISM: Fusarium

<400> SEQUENCE: 31

atatcgtgaa gatatgcggc attgatgcca cc                                   32


<210> SEQ ID NO 32
<211> LENGTH: 35
<212> TYPE: DNA
<213> ORGANISM: Fusarium

<400> SEQUENCE: 32

ggcggcaata accggccgaa cattccggat atccc                                35


<210> SEQ ID NO 33
<211> LENGTH: 32
<212> TYPE: DNA
<213> ORGANISM: Fusarium

<400> SEQUENCE: 33

cactgctatc accaacatgt ttactcaagt cc                                   32


<210> SEQ ID NO 34
<211> LENGTH: 32
<212> TYPE: DNA
<213> ORGANISM: Fusarium

<400> SEQUENCE: 34

ggacttgagt aaacatgttg gtgatagcag tg                                   32


<210> SEQ ID NO 35
<211> LENGTH: 29
<212> TYPE: DNA
<213> ORGANISM: Fusarium

<400> SEQUENCE: 35

gactcatgag gagctccctt gtgctgttc                                       29


<210> SEQ ID NO 36
<211> LENGTH: 34
<212> TYPE: DNA
<213> ORGANISM: Fusarium

<400> SEQUENCE: 36

tgattaatta acctaaagac atgtcccaat taac                                 34


<210> SEQ ID NO 37
<211> LENGTH: 25
<212> TYPE: DNA
<213> ORGANISM: Fusarium

<400> SEQUENCE: 37

gcatttaaat tactactgtg atgtg                                           25


<210> SEQ ID NO 38
<211> LENGTH: 25
<212> TYPE: DNA
<213> ORGANISM: Fusarium

<400> SEQUENCE: 38

gattgatgtg aaacacatgt tgatg                                           25


<210> SEQ ID NO 39
```

-continued

```
<211> LENGTH: 25
<212> TYPE: DNA
<213> ORGANISM: Fusarium

<400> SEQUENCE: 39

cgacccggga attagagagg ttagg                                    25


<210> SEQ ID NO 40
<211> LENGTH: 28
<212> TYPE: DNA
<213> ORGANISM: Fusarium

<400> SEQUENCE: 40

cgtataaccc atggtggact tgtcggac                                 28
```